(12) United States Patent
Fujiwara et al.

(10) Patent No.: US 10,368,841 B2
(45) Date of Patent: Aug. 6, 2019

(54) ULTRASOUND DIAGNOSTIC APPARATUS

(71) Applicant: Canon Medical Systems Corporation, Otawara-shi (JP)

(72) Inventors: Megumu Fujiwara, Sakura (JP); Kensuke Shinoda, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 671 days.

(21) Appl. No.: 14/478,678

(22) Filed: Sep. 5, 2014

(65) Prior Publication Data

US 2014/0378837 A1 Dec. 25, 2014

Related U.S. Application Data

(63) Continuation of application No. PCT/JP2013/056865, filed on Mar. 12, 2013.

(30) Foreign Application Priority Data

Mar. 12, 2012 (JP) .................................. 2012-054938
Mar. 12, 2013 (JP) .................................. 2013-049334

(51) Int. Cl.
*A61B 8/00* (2006.01)
*A61B 8/08* (2006.01)
*A61B 8/14* (2006.01)

(52) U.S. Cl.
CPC ............ *A61B 8/463* (2013.01); *A61B 8/0866* (2013.01); *A61B 8/4254* (2013.01); (Continued)

(58) Field of Classification Search
USPC ........................................................ 600/443
See application file for complete search history.

(56) References Cited

U.S. PATENT DOCUMENTS 6,500,118 B1* 12/2002 Hashimoto .............. A61B 8/00 128/916
2004/0122310 A1* 6/2004 Lim ......................... A61B 8/00 600/426

(Continued)

FOREIGN PATENT DOCUMENTS

JP 57-86335 A 5/1982
JP 2000-175910 A 6/2000

(Continued)

OTHER PUBLICATIONS

International Search Report dated Apr. 23, 2013 for PCT/JP2013 /056865 filed on Mar. 12, 2013 with English Translation.

(Continued)

*Primary Examiner* — Joel F Brutus
(74) *Attorney, Agent, or Firm* — Oblon, McClelland, Maier & Neustadt, L.L.P.

(57) ABSTRACT

An ultrasound diagnostic apparatus according to an embodiment includes an abdominal image generator, an ultrasonic image generation unit, a specifier, and a display controller. The abdominal image generator generates an abdominal image graphically representing the abdomen of a mother. The ultrasonic image generation unit generates an ultrasonic image based on a reflected wave signal received by an ultrasonic probe put on the abdomen of the mother. The specifier specifies the position of the ultrasonic probe on the abdominal image. The display controller causes superimposed display of the ultrasonic image on the position on the abdominal image thus specified in accordance with the echo direction of the ultrasonic probe.

20 Claims, 22 Drawing Sheets

(52) U.S. Cl.
CPC ............ *A61B 8/5223* (2013.01); *A61B 8/14* (2013.01); *A61B 8/4245* (2013.01); *A61B 8/464* (2013.01); *A61B 8/467* (2013.01); *A61B 8/483* (2013.01); *A61B 8/565* (2013.01)

(56) References Cited

U.S. PATENT DOCUMENTS

| | | | | |
|---|---|---|---|---|
| 2005/0251039 | A1* | 11/2005 | Chalana | A61B 5/204 600/437 |
| 2007/0073148 | A1* | 3/2007 | Kim | A61B 8/00 600/437 |
| 2010/0036242 | A1* | 2/2010 | Yuk | A61B 5/02014 600/437 |

FOREIGN PATENT DOCUMENTS

| | | |
|---|---|---|
| JP | 2007-020732 A | 2/2007 |
| JP | 2011-011001 A | 1/2011 |

OTHER PUBLICATIONS

International Written Opinion dated Apr. 23, 2013 for PCT/JP2013/056865 filed on Mar. 12, 2013.

\* cited by examiner

FIG.6

| | ORIENTATION OF PUTTING ULTRASONIC PROBE | DIRECTION OF ECHO | BASE IMAGE DISPLAYED |
|---|---|---|---|
| (A) | H-F(F-H) | L-R(R-L) | |
| (B) | A-P | R-L(L-R) | |
| (C) | H-F(F-H) | A-P | |
| (D) | L-R | A-P | |

FIG.18
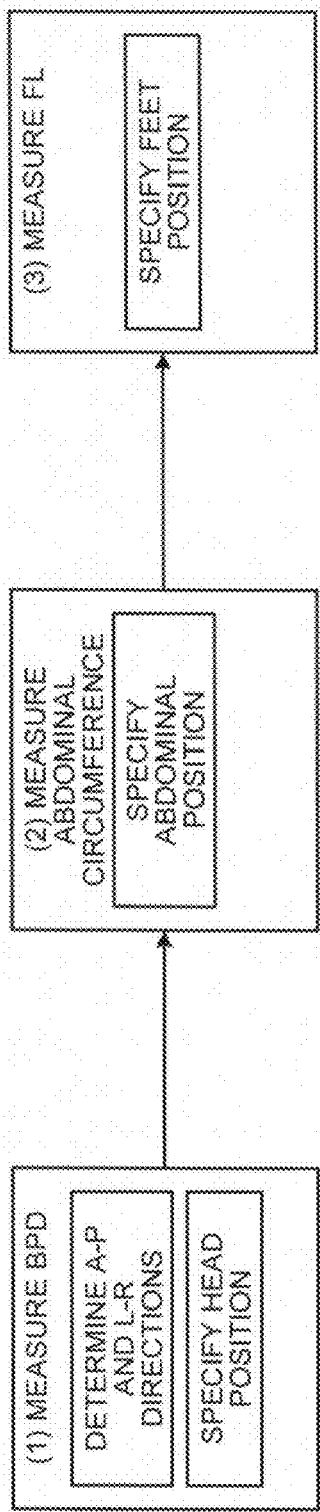
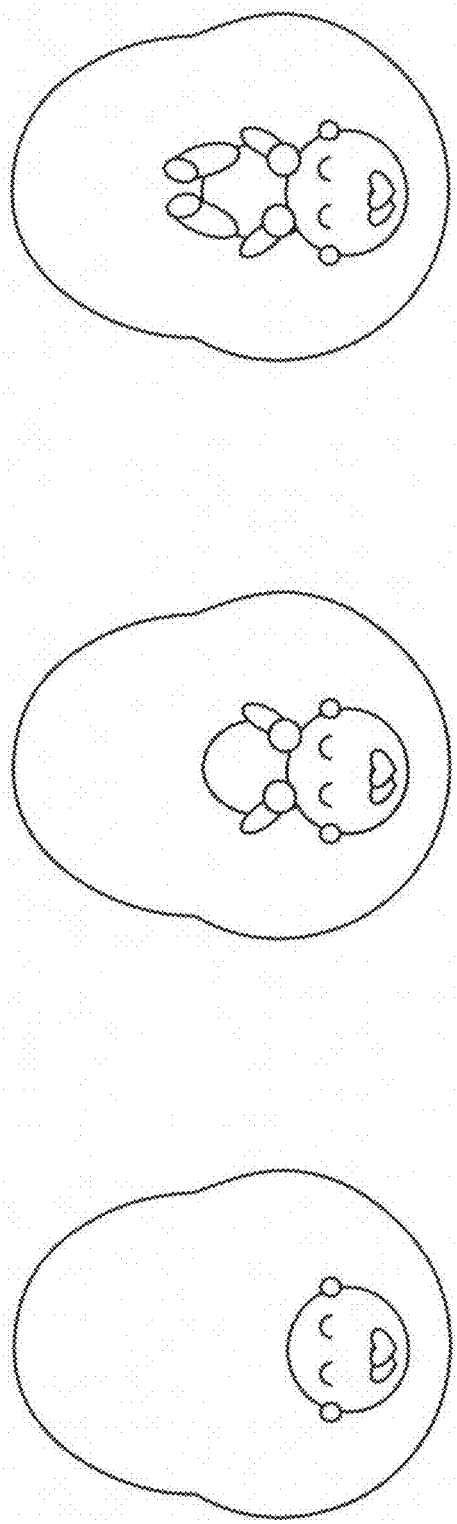

ULTRASOUND DIAGNOSTIC APPARATUS

CROSS-REFERENCE TO RELATED APPLICATIONS

This application is a continuation of International Application No. PCT/JP2013/056865, filed on Mar. 12, 2013 which claims the benefit of priority of the prior Japanese Patent Applications No. 2012-054938, filed on Mar. 12, 2012, and No. 2013-049334, filed on Mar. 12, 2013, the entire contents of which are incorporated herein by reference.

FIELD

Embodiments described herein relate generally to an ultrasound diagnostic apparatus.

BACKGROUND

An ultrasound diagnostic apparatus transmits an ultrasonic pulse to a biological body and receives a reflected wave thereof to apply the principle of pulse reflection to the reflected wave thus received, thereby generating an image of biological tissues. The ultrasound diagnostic apparatus has characteristics such as non-invasive and real-time display and is widely used in prenatal checkups.

Operators who do not have enough experience of radiogram interpretation find it difficult to grasp the position and the orientation of a fetus in a mother from an ultrasonic image displayed on a display (hereinafter, an echo image as appropriate). As a fetus grows large in late pregnancy, it becomes further difficult for operators who do not have enough experience of radiogram interpretation to grasp the position and the orientation of the fetus because its head and abdomen are partially displayed in one screen of the echo image. However, there are demands from pregnant women for grasping the position and the orientation of fetuses.

BRIEF DESCRIPTION OF THE DRAWINGS

FIG. 6 is a diagram illustrating determination of the direction of a viewpoint according to the first embodiment;

FIG. 18 is a diagram illustrating processing of superimposed display according to the second embodiment;

DETAILED DESCRIPTION

An ultrasound diagnostic apparatus according to an embodiment includes an abdominal image generator, an ultrasonic image generation unit, a specifier, and a display controller. The abdominal image generator generates an abdominal image graphically representing the abdomen of a mother. The ultrasonic image generation unit generates an ultrasonic image based on a reflected wave signal received by an ultrasonic probe put on the abdomen of the mother. The specifier specifies the position of the ultrasonic probe on the abdominal image. The display controller causes superimposed display of the ultrasonic image on the position on the abdominal image thus specified in accordance with the echo direction of the ultrasonic probe.

An ultrasound diagnostic apparatus according to embodiments will be explained with reference to accompanying drawings. However, the embodiments should not be limited to those described below. The contents described in each embodiment can also be similarly applied to other embodiments, in principle.

First Embodiment

Figure 1:
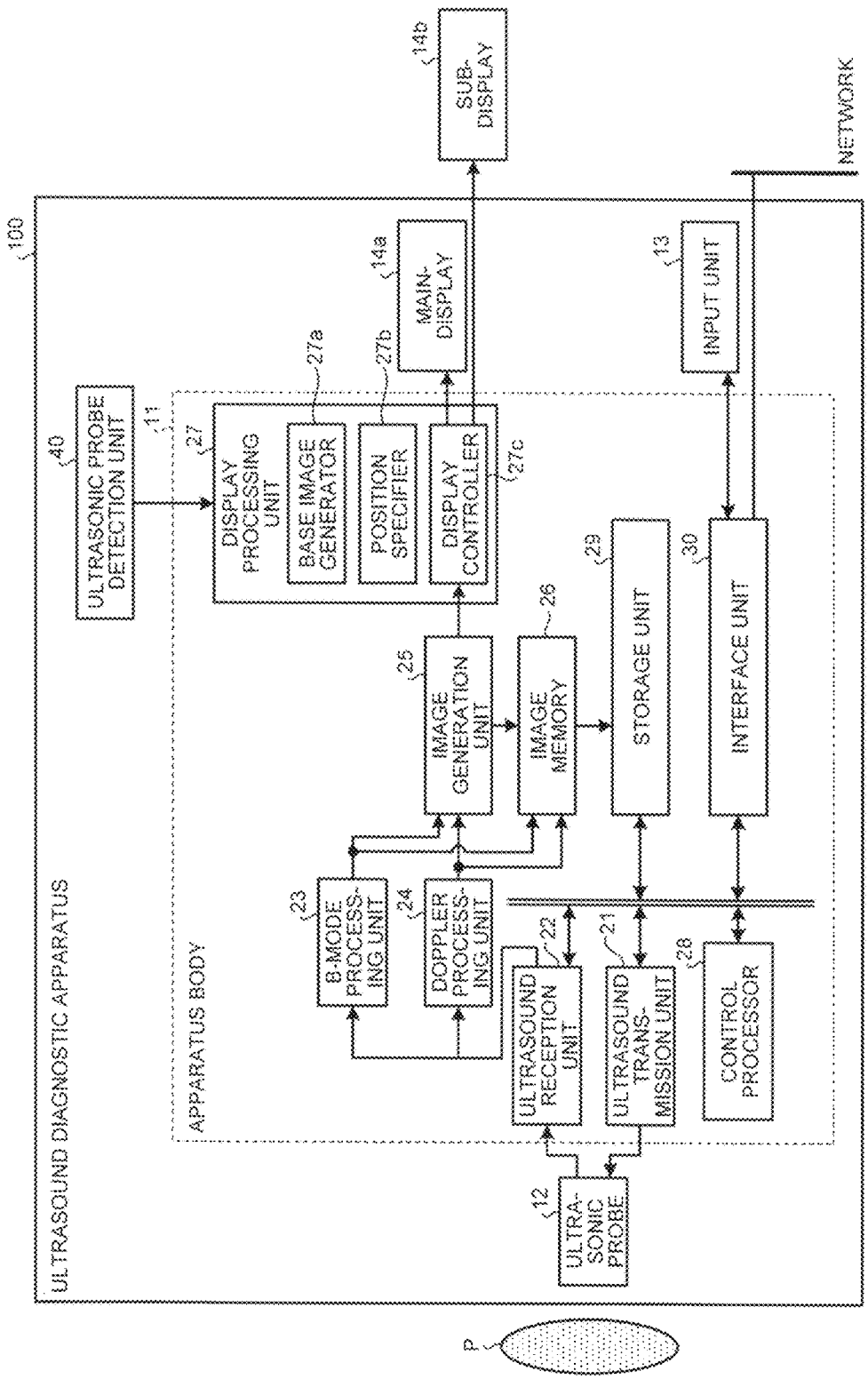
FIG. 1 is a functional block diagram of an ultrasound diagnostic apparatus according to a first embodiment.

FIG. 1 is a functional block diagram of an ultrasound diagnostic apparatus 100 according to a first embodiment.

As illustrated in FIG. 1, the ultrasound diagnostic apparatus 100 according to the first embodiment includes an apparatus body 11, an ultrasonic probe 12, an input unit 13, a main display 14a, and an ultrasonic probe detection unit 40. A subdisplay 14b may be provided separately from the ultrasound diagnostic apparatus 100 as illustrated in FIG. 1, or may be provided as part of the ultrasound diagnostic apparatus 100.

The ultrasonic probe 12 includes a plurality of piezoelectric transducer elements. The piezoelectric transducer elements generate ultrasonic pulses based on a drive signal supplied from an ultrasound transmission unit 21 described later and receive a reflected wave from a patient P to convert the reflected wave thus received into an electric signal. The ultrasonic probe 12 also includes matching layers provided to the piezoelectric transducer elements and backing materials preventing ultrasonic waves from traveling behind the piezoelectric transducer elements, for example.

When ultrasonic pulses are transmitted from the ultrasonic probe 12 to the patient P, the ultrasonic pulses thus transmitted are sequentially reflected on the planes of discontinuity of acoustic impedances in body tissues of the patient P and then received by the piezoelectric transducer elements included in the ultrasonic probe 12 as echo signals. The amplitudes of the echo signals thus received depend on the differences between the acoustic impedances on a plane of discontinuity on which the ultrasonic pulses are reflected. When the ultrasonic pulses transmitted are reflected on a moving blood flow or the surface of a cardiac wall, for example, the echo signals undergoes a frequency shift depending on the velocity component in the ultrasound transmission direction of the moving body because of the Doppler effect.

The input unit 13 includes a mouse, a keyboard, buttons, a panel switch, a touch command screen, a foot switch, or a track ball and is connected to the apparatus body 11. The input unit 13 receives various instructions and setting requests from the operator of the ultrasound diagnostic apparatus 100 and transmits the instructions and the setting requests thus received to the apparatus body 11.

The main display 14a displays a graphical user interface (GUI) through which the operator of the ultrasound diagnostic apparatus 100 inputs various instructions and setting requests using the input unit 13 and displays echo images generated by an image generation unit 25 described later. The echo images include a B-mode image, an M-mode image, a Doppler image (a color Doppler image, a pulse Doppler image, and the like) and present morphological information and blood flow information of a patient, for example.

The apparatus body 11 includes the ultrasound transmission unit 21, an ultrasound reception unit 22, a B-mode processing unit 23, a Doppler processing unit 24, the image generation unit 25, an image memory 26, a display processing unit 27, a control processor (Central Processing Unit: CPU) 28, a storage unit 29, and an interface unit 30. The ultrasound transmission unit 21, the ultrasound reception unit 22, and other units included in the apparatus body 11 are configured by hardware such as integrated circuits or by programs, depending on the case.

The ultrasound transmission unit 21 transmits ultrasonic pulses to the patient P. Specifically, the ultrasound transmission unit 21 includes a purse generator, a transmission delay unit, a pulsar, and the like and supplies a drive signal to the ultrasonic probe 12. The pulse generator repeatedly generates a rate pulse for forming an ultrasonic pulse at a predefined pulse repetition frequency (PRF). The PRF is also called a rate frequency (frHz). The transmission delay unit provides each rate pulse generated by the pulse generator with a transmission delay time for each piezoelectric transducer elements. The transmission delay time is required to converge ultrasonic pulses generated by the ultrasonic probe 12 into a beam to determine transmission directionality. The pulsar applies a drive signal (drive pulse) to the ultrasonic probe 12 at the timing based on the rate pulse. In other words, the transmission delay unit adjusts the transmission direction from the surface of the piezoelectric transducer elements as required by changing the transmission delay time provided to each rate pulse.

The ultrasound reception unit 22 receives echo signals from the patient P. Specifically, the ultrasound reception unit 22 includes a preamplifier, an analog/digital (A/D) converter, and a reception delay unit, and an adder, and performs various processing on the echo signals received by the ultrasonic probe 12. The preamplifier amplifies the echo signals for each channel to perform gain correction processing. The A/D converter A/D-converts the echo signals thus gain-corrected. The reception delay unit provides the echo signals with a reception delay time required to determine reception directionality. The adder performs addition processing on the echo signals provided with the reception delay time by the reception delay unit. The addition processing performed by the adder enhances reflection components along the direction in accordance with the reception directionality of the echo signals. The transmission and reception directionalities form an integrated reception beam of ultrasound transmission and reception. It should be noted various forms are selectable such as cases where the echo signals output from the ultrasound reception unit 22 are signals including phase information called radio frequency (RF) signals or signals including amplitude information after envelope demodulation processing, for example.

The B-mode processing unit 23 receives echo signals from the ultrasound reception unit 22 and performs logarithmic amplification, envelope demodulation, and the like to generate B-mode data. The B-mode data is data of each scan line in which the intensity of a signal is represented by the brightness of its luminance. The B-mode processing unit 23 transmits the B-mode data thus generated to the image generation unit 25.

The Doppler processing unit 24 receives the echo signals from the ultrasound reception unit 22 and performs frequency analysis of the blood velocity on the echo signals thus received to generate Doppler data. The Doppler data is generated by extracting blood flow component, tissue component, and contrast agent echo component that are affected by the Doppler effect and further extracting moving body information, such as average velocity, variance, and power at multiple points from the components thus extracted. The Doppler processing unit 24 transmits the Doppler data thus generated to the image generation unit 25.

The image generation unit 25 generates an echo image from the B-mode data generated by the B-mode processing unit 23 and the Doppler data generated by the Doppler processing unit 24. Specifically, the image generation unit 25 generates an echo image as a displayed image through conversion (scan-conversion) of data of a plurality of scan lines included in the B-mode data into data of scan lines in a video format represented by television.

The image generation unit 25 generates a B-mode image from the B-mode data, for example. The image generation unit 25 also generates an average velocity image, a variance image, a power image and a combination image thereof as a Doppler image from the Doppler data. It should be noted the data before input to the image generation unit 25 is called "raw data" in some cases.

The image memory 26 stores therein the B-mode data generated by the B-mode processing unit 23, the Doppler data generated by the Doppler processing unit 24, and the echo image generated by the image generation unit 25. For example, the operator can call up the images stored during the test to use the images as still images or reproduce a plurality of images as moving images.

The display processing unit 27 processes the echo image generated by the image generation unit 25 with various processing such as dynamic range, luminance, contrast, gamma curve correction, RGB conversion, and the like and causes the main display 14a to display the echo image thus processed. For example, the display processing unit 27 causes the main display 14a to display the B-mode image generated by the image generation unit 25. The display processing unit 27 also causes the main display 14a to perform color display of the Doppler image generated by the image generation unit 25, for example. The display processing unit 27 according to the present embodiment includes a base image generator 27a, a position specifier 27b, and a display controller 27c. The details of the display processing unit 27 will be described later.

The control processor 28 has a function as an information processing apparatus (calculator) and controls the overall processing performed by the ultrasound diagnostic apparatus 100. Specifically, the control processor 28 controls processing performed by the ultrasound transmission unit 21, the ultrasound reception unit 22, the B-mode processing unit 23, the Doppler processing unit 24, the image generation unit 25, and the display processing unit 27 based on various instructions and setting requests input by the operator through the input unit 13 and various computer programs and setting information read from the storage unit 29.

The storage unit 29 stores therein various data such as apparatus control programs for performing transmission and reception of ultrasonic waves, image processing, and display processing; diagnostic information (patients' IDs and doctors' opinions, for example); a diagnostic protocol; and various setting information. The storage unit 29 is also used for storing the images stored by the image memory 26 as necessary. The data stored in the storage unit 29 can be transferred to an external peripheral device through the interface unit 30.

The interface unit 30 is an interface related to the input unit 13 and an external peripheral device (not illustrated). The interface unit 30 can transfer data and analysis results such as an echo image acquired by the ultrasound diagnostic apparatus 100 to other devices through a network.

The ultrasonic probe detection unit 40 detects the position and the angle of the ultrasonic probe 12. The details of the ultrasonic probe detection unit 40 will be described later. The subdisplay 14b is provided separately from the main display 14a of the ultrasound diagnostic apparatus 100 and includes a display for a tablet terminal, for example.

Figure 2:
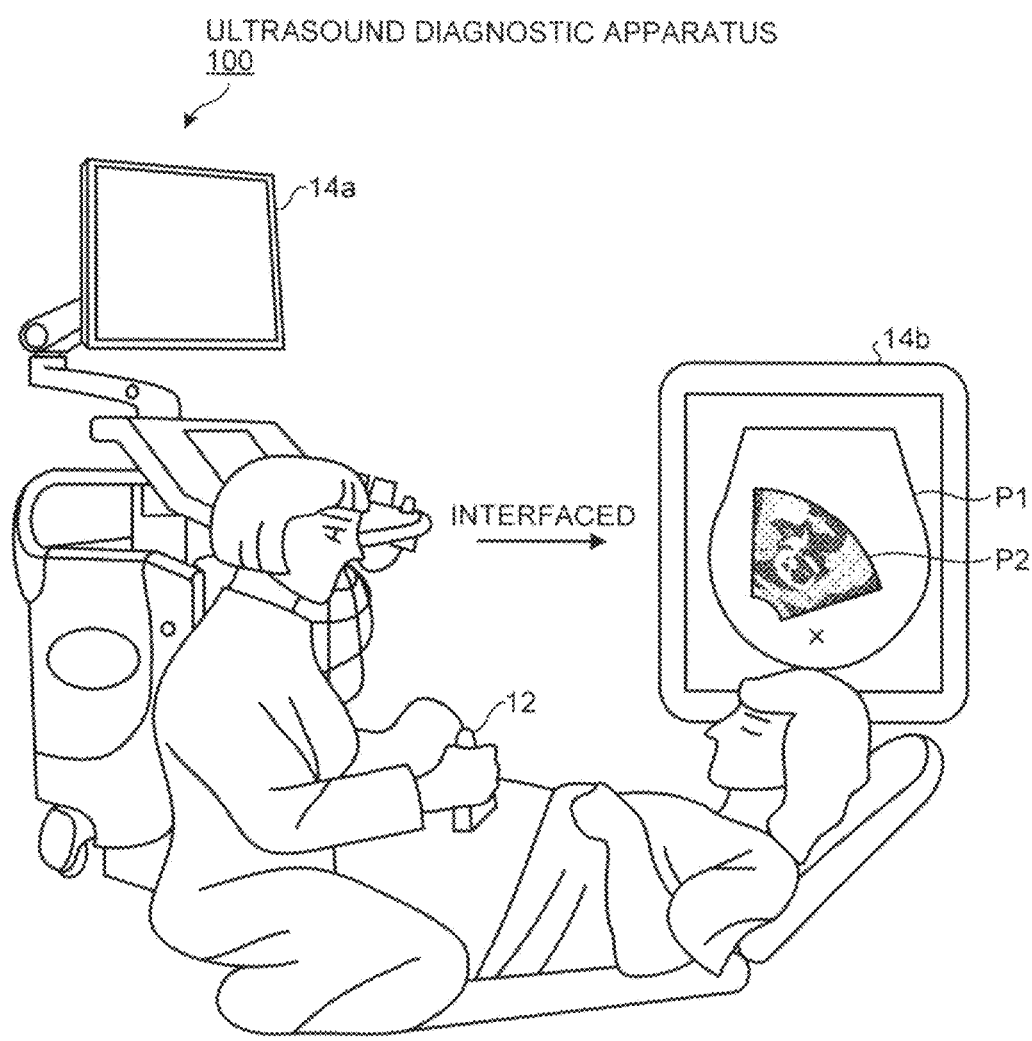
FIG. 2 is a diagram illustrating display of an echo image according to the first embodiment.

FIG. 2 is a diagram illustrating display of an echo image according to the first embodiment. When displaying an echo image collected by the ultrasonic probe 12 put on the abdomen of a mother, the ultrasound diagnostic apparatus 100 according to the first embodiment performs superimposed (combined) display of the echo image on the abdomen image (hereinafter, referred to as "base image" as appropriate) graphically representing the abdomen of the mother, as illustrated in FIG. 2. For example, the ultrasound diagnostic apparatus 100 according to the first embodiment is inter- faced to the subdisplay 14b to cause the subdisplay 14b to perform superimposed display of an echo image P2 on a base image P1, as illustrated in FIG. 2. With this display system, even operators who do not have enough experience of radiogram interpretation can easily grasp the position and the orientation of a fetus in an abdomen. On the main display 14a, the ultrasound diagnostic apparatus 100 may display ordinary echo images. For example, the operator of the ultrasound diagnostic apparatus 100 may observe the ordinary echo images displayed on the main display 14a. In addition, the embodiments should not be limited thereto. Superimposed display of the echo image P2 on the base image P1 may be performed on the main display 14a with the subdisplay 14b unused or may be performed on the both displays, for example.

The display processing described above is performed by the display processing unit 27. Back to FIG. 1, the display processing unit 27 includes the base image generator 27a, the position specifier 27b, and the display controller 27c. Based on measurement information of the abdomen of the mother, the base image generator 27a generates the base image graphically representing the abdomen of the mother. The position specifier 27b specifies the position of the ultrasonic probe 12 on the base image. The display controller 27c performs superimposed display of the echo image on the position on the base image specified by the position specifier 27b in accordance with the echo direction of the ultrasonic probe 12.

Figure 3:
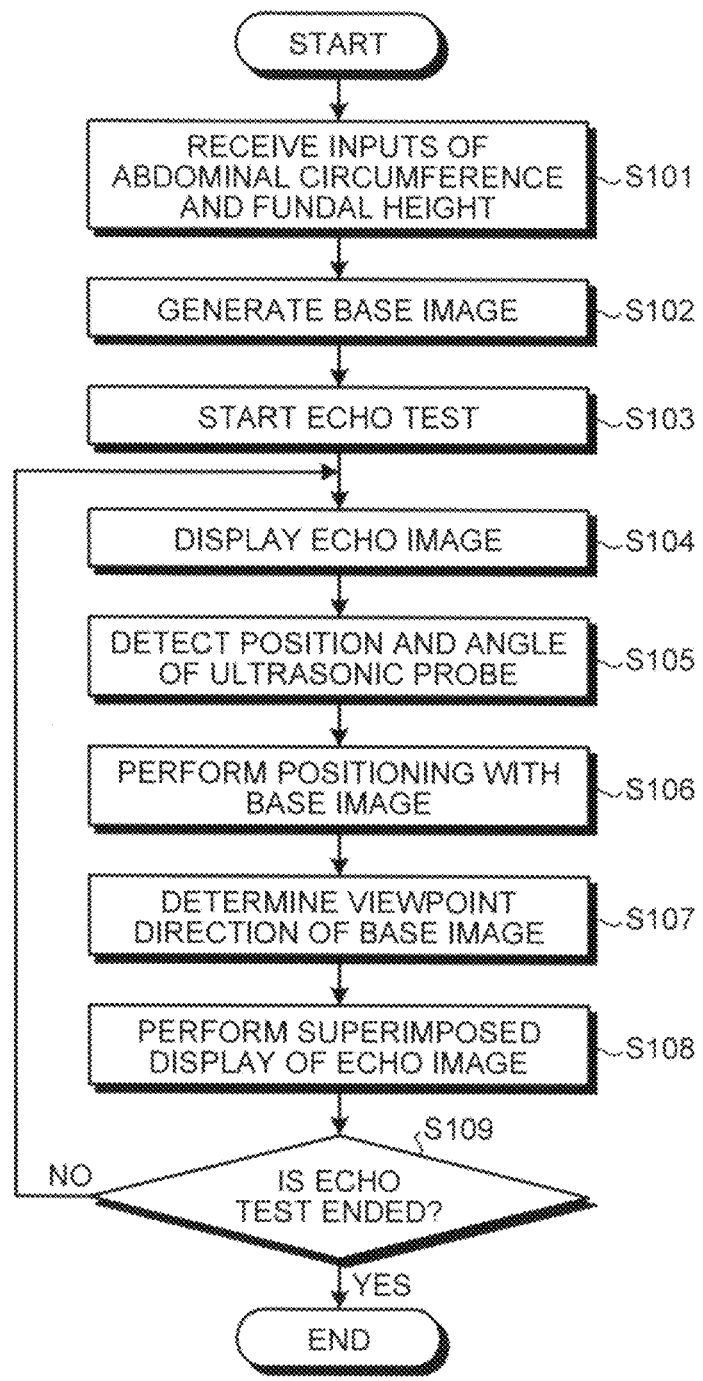
FIG. 3 is a flow chart illustrating the procedure of display processing according to the first embodiment.
Figure 4:
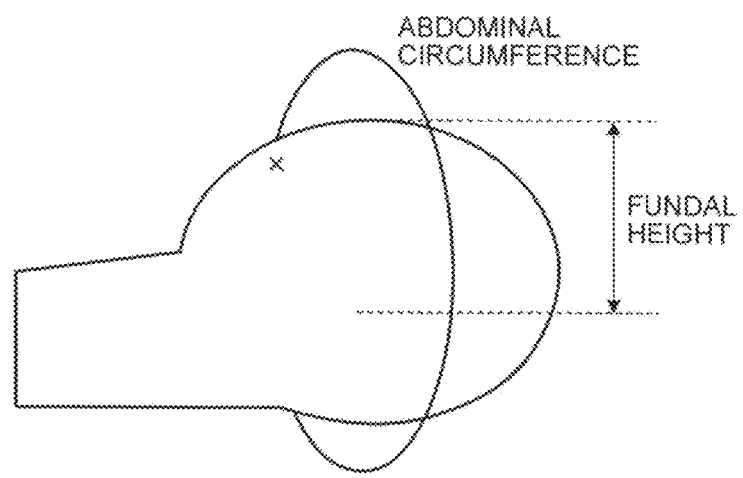
FIG. 4 is a diagram illustrating measurement information of the abdomen of a mother according to the first embodiment.

FIG. 3 is a flow chart illustrating the procedure of display processing according to the first embodiment. First, the base image generator 27a receives an input of measurement information of the abdomen of the mother (Step S101). FIG. 4 is a diagram illustrating measurement information of the abdomen of the mother according to the first embodiment. The measurement information of the abdomen of the mother includes the abdominal circumference and the fundal height generally acquired in a prenatal checkup as illustrated in FIG. 4. The base image generator 27a receives inputs of the abdominal circumference and the fundal height measured in a prenatal checkup through the input unit 13 or a network, for example.

Next, the base image generator 27a generates the base image graphically representing the abdomen of the mother based on the input of the measurement information of the abdomen received at Step S101 (Step S102). For example, the base image generator 27a stores therein in advance a three-dimensional base image model as a reference base image, and adjust the abdominal circumference and the fundal height of this base image model based on the abdominal circumference and the fundal height received as the measurement information unique to the mother to be tested. This procedure generates a base image similar to the actual abdomen. It should be noted the base image and the image graphically represented like a fetus image described later are also called a scheme.

Figure 5:
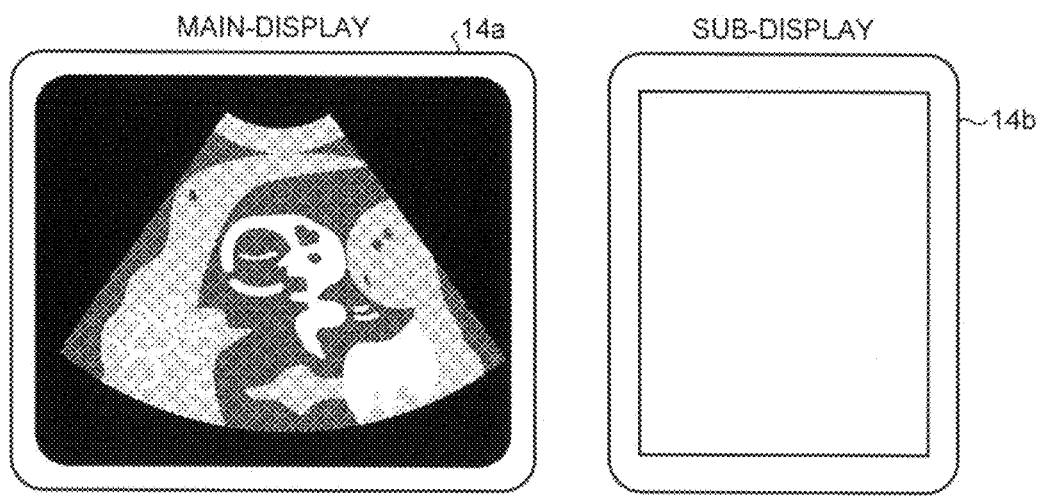
FIG. 5 is a diagram illustrating display of an echo image in the first embodiment.

Next, an echo test is started using the ultrasound diagnostic apparatus 100 in accordance with the operation performed by the operator (Step S103). As explained above with reference to FIG. 2, the operator puts the ultrasonic probe 12 on the abdomen of the mother to be tested and starts the echo test, for example. Then, the image generation unit 25 generates an echo image in real time and the display controller 27c controls the main display 14a to display the echo image generated by the image generation unit 25 in real time (Step S104). FIG. 5 is a diagram illustrating display of an echo image in the first embodiment. In this case, the main display 14a displays the echo image in real time and the subdisplay 14b displays no image under the control of the display controller 27c at Step S104.

The ultrasonic probe detection unit 40 detects the position and the angle of the ultrasonic probe 12 put on the abdomen of the mother (Step S105). The ultrasonic probe detection unit 40 may detect the position and the angle of the ultrasonic probe 12 using a known technology. To explain one example, the ultrasonic probe detection unit 40 includes a transmitter, a position sensor, and a signal processor, for example. The transmitter is placed on an optional position and forms a three-dimensional magnetic field extended to the outside while centering on itself. The position sensor is mounted on the surface of the ultrasonic probe 12 and detects the three-dimensional magnetic field formed by the transmitter. The position sensor converts information of the magnetic field thus detected into signals and outputs the signals to the signal processor. The signal processor calculates the coordinates (position) and the orientation (angle) of the position sensor in a space with its origin at the transmitter based on the signals received from the position sensor.

Next, the position specifier 27b specifies the position of the ultrasonic probe 12 on the base image based on the position of the ultrasonic probe 12 detected at Step S105 (Step S106). This is based on the assumption that the ultrasonic probe detection unit 40 has completed the position and scale adjustments between the coordinate system in the space with its origin at the transmitter and the coordinate system on the base image through prior adjustments using a known technology.

Next, the display controller 27c determines the direction of the viewpoint of the base image based on the angle of the ultrasonic probe 12 detected at Step S105 (Step S107). Specifically, the display controller 27c changes the direction of the viewpoint of the base image in a manner that a sectoral echo image (sectional image) is constantly displayed. Because the angle of the ultrasonic probe 12 represents the direction of the echo (image surface of the echo image), the display controller 27c calculates the direction perpendicular to the direction of the echo and rotates the base image generated at Step S102 along the orientation observed from the direction thus calculated, for example.

FIG. 6 is a diagram illustrating determination of the direction of a viewpoint according to the first embodiment. In FIG. 6, "H" represents the direction of the head, "F" represents the direction of the feet, "A" represents the abdomen side, "P" represents the back side, "R" represents the right direction, and "L" represents the left direction. For example, in the case of (A) in FIG. 6, the display controller 27c specifies that the longitudinal direction of the contact face of the ultrasonic probe 12 is along the direction of H-F (or F-H) and the direction of the echo is along the direction of L-R (or R-L) based on the angle information of the ultrasonic probe 12 received from the ultrasonic probe detection unit 40. In this case, because the display controller 27c rotates the base image along the direction illustrated in (A) in FIG. 6, the image surface of the sectoral echo image superimposed on the base image is displayed at the same angle as that of the display surface. As a result, the observer can easily observe the echo image.

In the case of (B) in FIG. 6, the display controller 27c specifies that the longitudinal direction of the contact face of the ultrasonic probe 12 is along the direction of A-P and the direction of the echo is along the direction of R-L (or L-R) based on the angle information of the ultrasonic probe 12 received from the ultrasonic probe detection unit 40. In this case, because the display controller 27c rotates the base image along the direction illustrated in (B) in FIG. 6, the image surface of the sectoral echo image superimposed on the base image is again displayed at the same angle as that of the display surface. In the case of (C) in FIG. 6, the display controller 27c specifies that the longitudinal direction of the contact face of the ultrasonic probe 12 is along the direction of H-F (or F-H) and the direction of the echo is along the direction of A-P based on the angle information of the ultrasonic probe 12 received from the ultrasonic probe detection unit 40. In this case, because the display controller 27c rotates the base image along the direction illustrated in (C) in FIG. 6, the image surface of the sectoral echo image superimposed on the base image is again displayed at the same angle as that of the display surface. In the case of (D) in FIG. 6, the display controller 27c specifies that the longitudinal direction of the contact face of the ultrasonic probe 12 is along the direction of L-R and the direction of the echo is along the direction of A-P based on the angle information of the ultrasonic probe 12 received from the ultrasonic probe detection unit 40. In this case, because the display controller 27c rotates the base image along the direction illustrated in (D) in FIG. 6, the image surface of the sectoral echo image superimposed on the base image is again displayed at the same angle as that of the display surface.

In the first embodiment, the display controller 27c controls the base image to be displayed with the direction of the feet and the back side positioned at the bottom of the screen so that the orientation of the abdomen of the mother can be easily grasped. The display controller 27c also controls the base image to be displayed with marks of soles added so that the orientation of the abdomen of the mother can be easily grasped. Specifically, in (B) and (D) in FIG. 6, the marks of "soles" are displayed, indicating that the direction of the viewpoint is along F to H, that is, looking up from the feet to the head.

Figure 7:
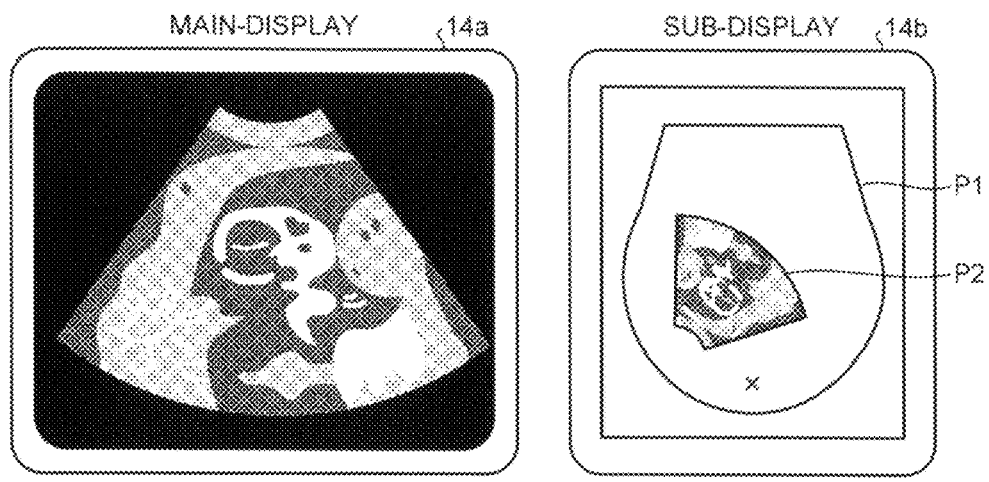
FIG. 7 is a diagram illustrating display of the echo image according to the first embodiment.

Furthermore, the display controller 27c performs superimposed display of the echo image in accordance with and employing the direction of the echo specified at Step S107 in the position of the ultrasonic probe 12 specified at Step S106 on the base image rotated at Step S107 (Step S108). FIG. 7 is a diagram illustrating display of the echo image according to the first embodiment. As illustrated in FIG. 7, the display controller 27c controls the main display 14a to display the ordinary echo image in real time and controls the subdisplay 14b to perform superimposed display of the echo image P2 on the base image P1.

Until the echo test is completed (No at Step S109), processing from Step S104 to Step S108 is repeated. In conjunction with the scanning performed by the ultrasonic probe 12, displays on the main display 14a and the subdisplay 14b are changed in real time. Specifically, the image generation unit 25 sequentially generates echo images in conjunction with the moves of the ultrasonic probe 12 and the position specifier 27b sequentially specifies the positions of the ultrasonic probe 12 on the base image in conjunction with the move of the ultrasonic probe 12. The display controller 27c performs superimposed display of the echo images thus generated sequentially in accordance with and employing the direction of the echo of the ultrasonic probe 12 on the positions thus specified sequentially on the base image.

As described above, the first embodiment enables superimposed display of an echo image on the position on the base image corresponding to the actual position, allowing even operators who do not have enough experience of radiogram interpretation to easily grasp the position and the orientation of a fetus in an abdomen.

In other words, the ultrasound diagnostic apparatus 100 according to the embodiment provides a pregnant woman with the position and the orientation of a fetus in an abdomen in real time along with an echo image, so that the woman can grasp the position and the orientation easily and intuitively. As a result, explanation of the fetus is easy for the operator. In the first embodiment, the subdisplay 14b is provided for the display so that the operation performed by the operator will not be hindered.

Figure 8:
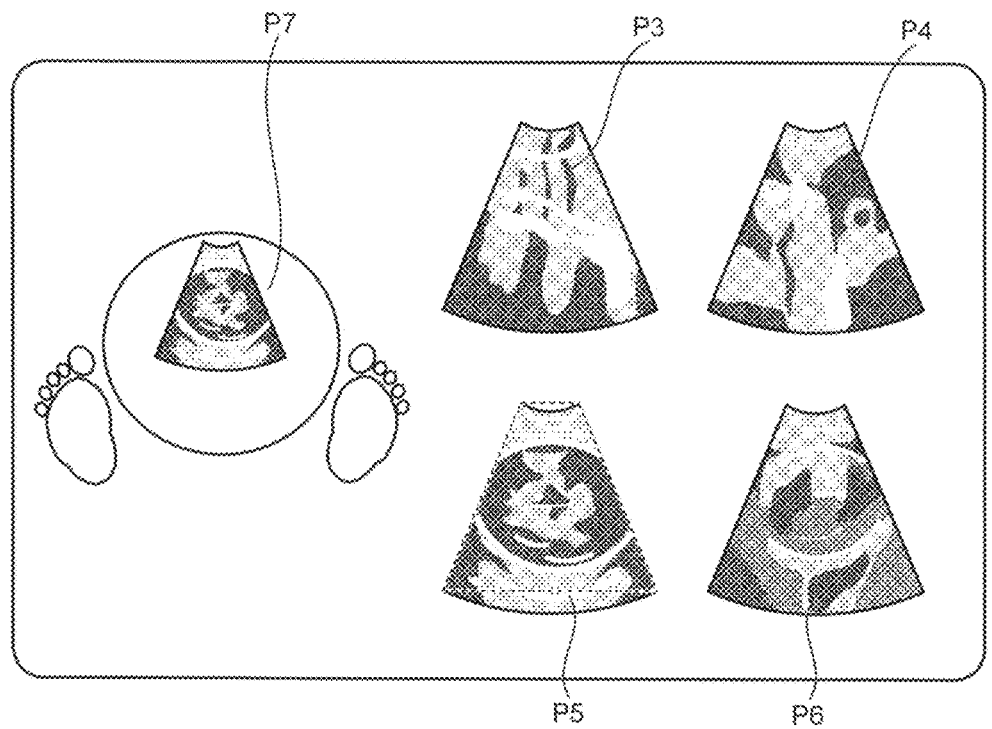
FIG. 8 is a diagram illustrating another example of display of the echo image according to the first embodiment.

Described above is the method with which the display controller 27c performs superimposed display of an echo image on the base image in real time, but the embodiments should not be limited thereto. FIG. 8 is a diagram illustrating another example of display of the echo image according to the first embodiment. During the echo test, the ultrasound diagnostic apparatus 100 may take a still image of the echo image. For example, P3 illustrated in FIG. 8 is a still image of the feet of the fetus in the mother, P4 is a still image of the face of the fetus, P5 is a still image of the head of the fetus, and P6 is a still image of the abdomen of the fetus.

For example, the display controller 27c causes the subdisplay 14b to display a plurality of still images taken and generated during the echo test and, when the operator of the subdisplay 14b selects one image from the still images, the display controller 27c performs superimposed display of the still image thus selected on the base image. For example, when the operator selects the still image P5 (the dotted frame indicates the selection in FIG. 8), the display controller 27c causes superimposed display of this sill image P5 on the base image P7, as illustrated in FIG. 8.

In other words, the image generation unit 25 generates a still image of the echo image, the position specifier 27b specifies the position of the ultrasonic probe 12 at the time when the still image was taken, and the display controller 27c performs superimposed display of the still image on the position thus specified on the base image upon receiving a display instruction of the echo image. The display controller 27c may change the direction of the viewpoint of the base image for display of this still image in a manner that a sectoral sectional view of the echo image is constantly displayed, similarly to the case of the superimposed display of the echo image in real time.

It can be assumed that images used for measurement and observation of the fetus are used as a plurality of still images. This kind of display is effective in the case of a fetus in late pregnancy, which has become so large that the entire body thereof cannot be covered in one screen of the echo image.

Second Embodiment

A second embodiment will now be described. The first embodiment has described an example of superimposed display of an echo image in real time performed on a base image graphically representing the abdomen of a mother, but the embodiments should not be limited thereto. The second embodiment will describe an example of display where a base image is superimposed with a fetus image and probe images and echo images are displayed next to the image thus superimposed. The fetus image is an image graphically representing the fetus and the probe image is an image graphically representing the ultrasonic probe. For example, in the case of a fetus in late pregnancy, which has become so large that the entire body thereof cannot be covered in one screen of the echo image, a plurality of still images may be taken. In such a case, it is further difficult to grasp the relationship between the position of the fetus in the abdomen and the echo image. However, the ultrasound diagnostic apparatus 100 according to the second embodiment displays the position of the fetus in the abdomen and the echo image so that the relationship therebetween can be easily grasped.

Figure 9:
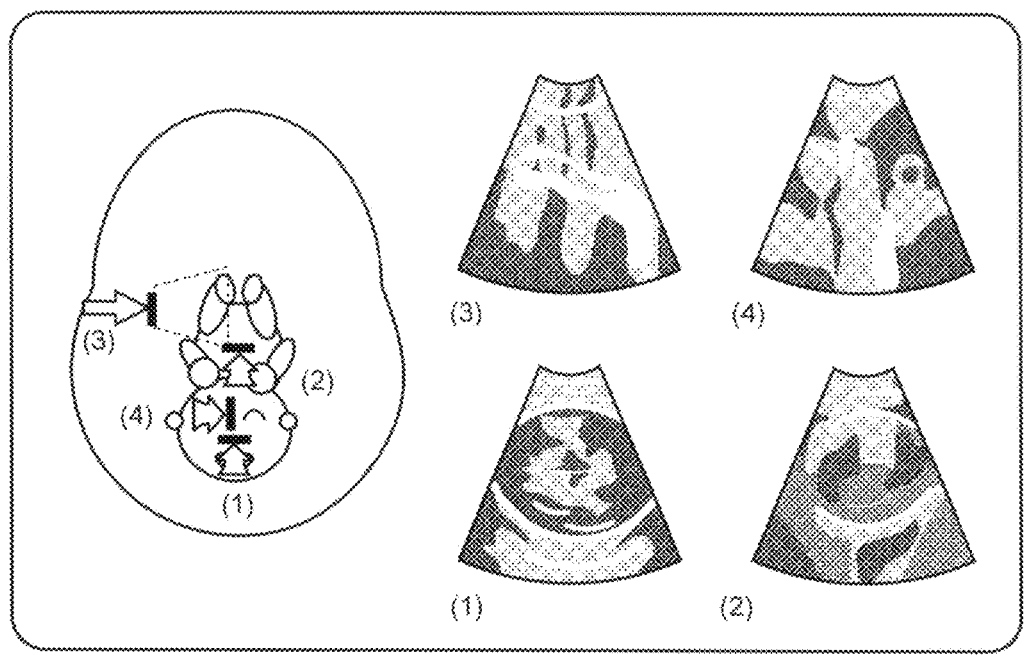
FIG. 9 is a diagram illustrating display of an echo image according to a second embodiment.

FIG. 9 is a diagram illustrating display of an echo image according to the second embodiment. For example, the ultrasound diagnostic apparatus 100 according to the second embodiment causes one screen on the subdisplay 14b to display a plurality of still images next to the base image as illustrated in FIG. 9. The ultrasound diagnostic apparatus 100 also performs superimposed display of a fetus image and probe images on the base image, as illustrated in FIG. 9. The ultrasound diagnostic apparatus 100 causes the fetus image to be placed on the base image in a manner that the position and the orientation of the fetus on the image are consistent with those of the actual fetus in the abdomen of the mother. The ultrasound diagnostic apparatus 100 also causes the probe images to be placed on the base image in a manner that the probe images indicate the imaging positions and the imaging directions of the still images. The second embodiment describes a case where both the fetus image and the probe images are displayed. However, the embodiments should not be limited to this, and cases where either one of them is displayed may be acceptable.

In FIG. 9, the numbers such as (1) indicate the correspondence between the still images and the probe images. The probe images (1), (2), and (4) indicate that the ultrasonic probe 12 is put on the abdomen from the perpendicular directions, and the probe image (3) indicates that the ultrasonic probe 12 is put on the abdomen from the side. The differences in the orientations of the ultrasonic probe 12 are represented by the differences in the arrow types, the presence or absence of the sector (dotted line in FIG. 9), and the like. All of the still images on the right are displayed in the same direction in FIG. 9, but the still images may be displayed in a manner that they are rotated in accordance with the respective echo directions, for example (such as rotating the still image (3) leftward by 90 degrees for display, for example).

In general, a plurality of still images are taken during the echo test in late pregnancy and the still images thus taken are used for measurement of the fetus. For example, a still image of the head of the fetus (see (1) in FIG. 9) is taken to be used for measurement of the biparietal diameter (BPD) of the fetus. For another example, a still image of the abdomen of the fetus (see (2) in FIG. 9) is taken to be used for measurement of the abdominal circumference of the fetus. For still another example, a still image of the feet of the fetus (see (3) in FIG. 9) is taken to be used for measurement of the fetal femur length (FL) of the fetus. When a still image of the face of the fetus (see (4) in FIG. 9) is taken, for example, it is checked for any abnormality. In addition to the face of the fetus, the spinal cord and the four limbs are imaged for checking for any abnormality, in some cases.

In the ultrasound diagnostic apparatus 100 according to the second embodiment, the display controller 27c specifies the positions of the regions of the fetus on the base image based on the measurement information described above and the position of the ultrasonic probe 12 specified on the base image, and performs superimposed display of the fetus image and the probe images on the base image.

Figure 10:
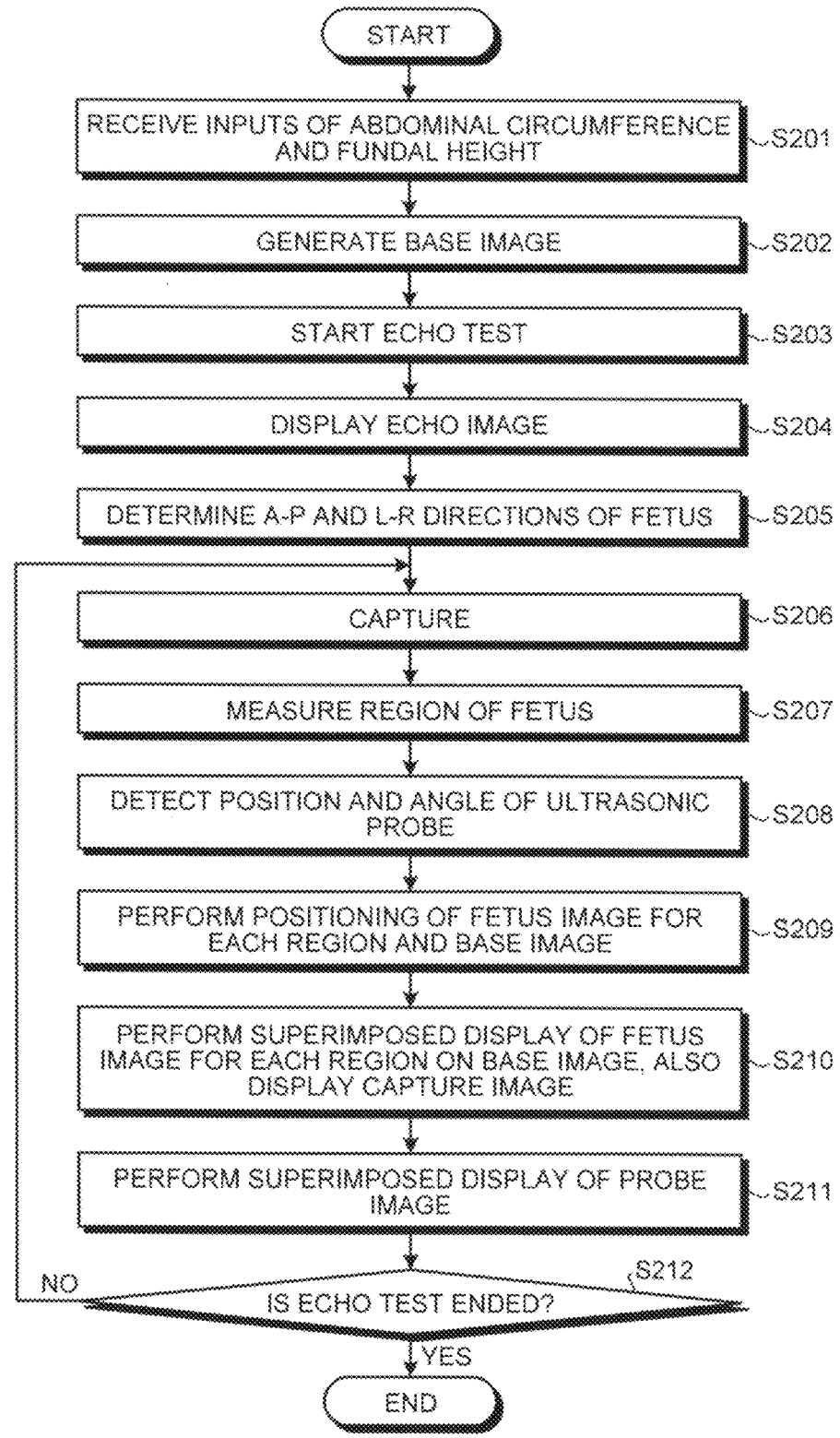
FIG. 10 is a flowchart illustrating the procedure of display processing according to the second embodiment.

FIG. 10 is a flowchart illustrating the procedure of display processing according to the second embodiment. First, the base image generator 27a receives an input of measurement information of the abdomen of the mother similarly to the first embodiment (Step S201). Next, the base image generator 27a generates the base image graphically representing the abdomen of the mother based on the measurement information of the abdomen received at Step S201 similarly to the first embodiment (Step S202).

Next, the echo test performed by the ultrasound diagnostic apparatus 100 is started in accordance with operation performed by the operator (Step S203). Thereafter, the image generation unit 25 generates an echo image in real time, and the display controller 27c causes the main display 14a to display the echo image thus generated by the image generation unit 25 in real time (Step S204).

For example, the operator first puts the ultrasonic probe 12 on the abdomen of the mother to be tested to observe the head of the fetus. The operator takes a still image of the head to measure the BPD of the fetus, for example, at which time the operator slides the ultrasonic probe 12 back and forth to adjust the imaging position. Because the ultrasound diagnostic apparatus 100 generates the echo image of the head of the fetus in real time, the display controller 27c performs imaging processing of this echo image, thereby determining the A-P direction and the L-R direction of the fetus relative to the abdomen (Step S205). The A-P direction and the L-R direction of the fetus are used for the display controller 27c to later place the fetus image on the base image.

Figure 11:
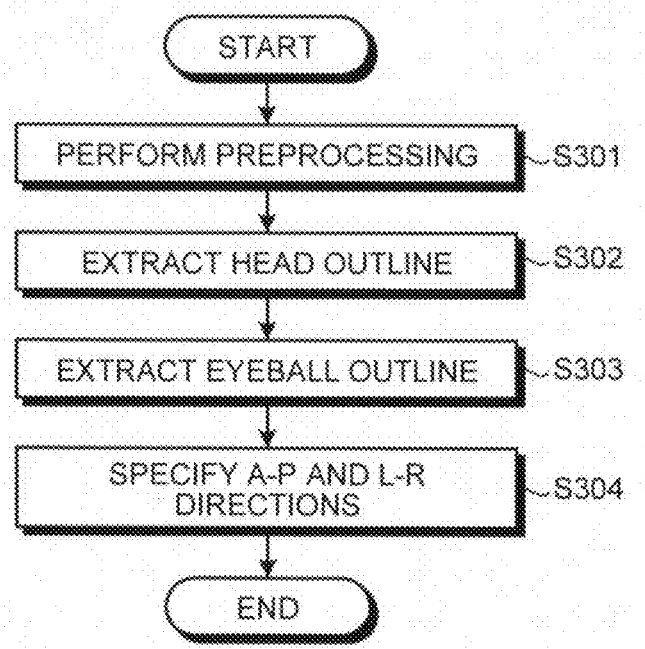
FIG. 11 is a flowchart illustrating the procedure of determination processing of the direction of a fetus according to the second embodiment.
Figure 12:
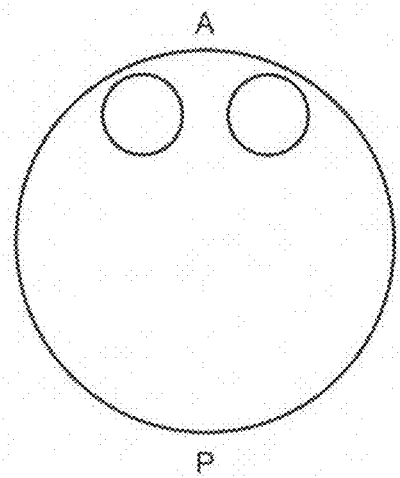
FIG. 12 is a diagram illustrating determination of the direction of a fetus according to the second embodiment.

FIG. 11 is a flowchart illustrating the procedure of determination processing of the direction of the fetus according to the second embodiment. FIG. 12 is a diagram illustrating determination of the direction of the fetus according to the second embodiment. In the second embodiment, the procedure of the processing illustrated in FIG. 11 is performed in real time on the echo image being taken in real time until the A-P direction and the L-R direction are specified during observation of the head of the fetus.

The display controller 27c first performs preprocessing such as smoothing and sharpening on the echo image to emphasize the head and the eyeballs of the fetus (Step S301). The display controller 27c then extracts the head outline from the echo image (Step S302). For the extraction of the head outline, a known technique may be used. For example, the display controller 27c may extract the head outline using an image processing technique for performing binarization on the echo image. The display controller 27c may also extract the head outline using an imaging processing technique for combining conditions such as the size and the degree of circularity to be applied to a dynamic outline model set to form the head geometry. When the head outline cannot be extracted due to the echo image being for the feet, not the head, the display controller 27c does not perform the processing at and after Step S303 and starts with the processing at Step S301 for the next echo image.

The display controller 27c then extracts the outlines of the eyeballs from the echo image (Step S303). Similarly to the extraction of the head outline, a known technique may be used for this extraction of the eyeballs. Because the fetus has two eyeballs, the display controller 27c extracts two eyeball outlines. Similarly to Step S302, when the eyeball outlines cannot be extracted, the display controller 27c does not perform the processing at and after Step S304 and starts with the processing at Step S301 for the next echo image.

As the head outline and the eyeball outlines are thus extracted, the display controller 27c specifies the A-P direction and the L-R direction of the fetus (Step S304). For example, the display controller 27c specifies the direction in which two eyeballs are positioned in the head to A (abdominal side) and specifies the direction in which two eyeballs are not positioned to P (back side), as illustrated in FIG. 12. The display controller 27c also specifies the R-L direction in accordance with the A-P direction.

Figure 13:
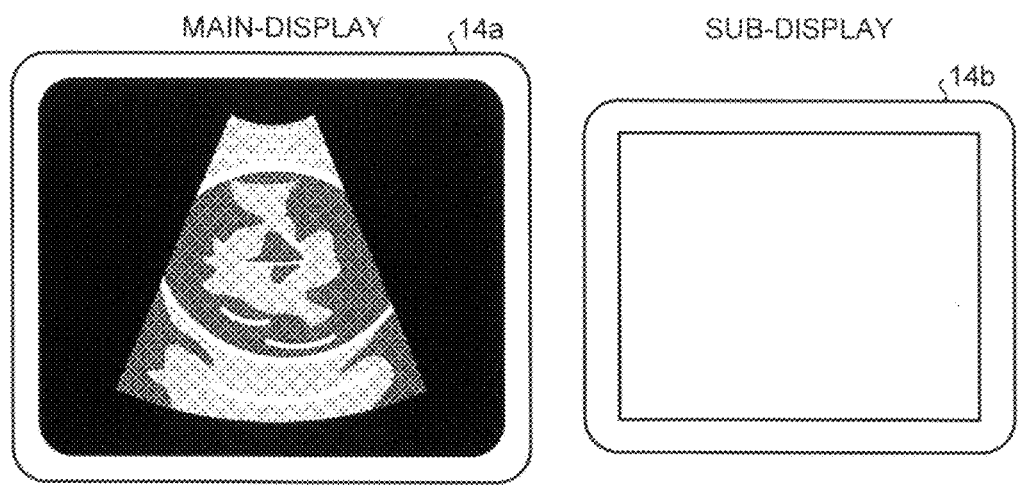
FIG. 13 is a diagram illustrating display of an echo image according to the second embodiment.

Back to FIG. 10, the operator takes a plurality of still images sequentially. For example, the ultrasound diagnostic apparatus 100 takes the image of the head among the regions of the fetus and capture a still image therefrom (S206). FIG. 13 is a diagram illustrating display of an echo image according to the second embodiment. At Step S206 in this case, the display controller 27c causes the main display 14a to display the echo image thus captured and the subdisplay 14b to display no images.

Figure 14:
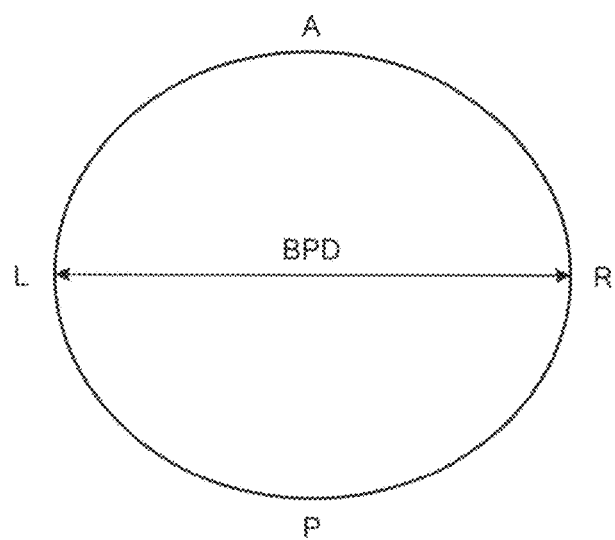
FIG. 14 is a diagram illustrating measurement of the biparietal diameter (BPD) according to the second embodiment.

Thereafter, the operator performs measurement of a region of the fetus using the still image (Step S207). For example, when the operator inputs a parameter name (BPD, abdominal circumference, LF, or the like) to the ultrasound diagnostic apparatus 100, the ultrasound diagnostic apparatus 100 causes the main display 14a to display a measurement tool (ruler, circle, or the like) suitable for the parameter name. The operator uses this measurement tool to measure the region of the fetus and inputs measurement information (values for the start and end points of the ruler, for example) to the ultrasound diagnostic apparatus 100. FIG. 14 is a diagram illustrating measurement of the biparietal diameter (BPD) according to the second embodiment. As illustrated in FIG. 14, the operator inputs the start point and the end point of the biparietal diameter on the still image of the head displayed on the main display 14a, for example. The ultrasound diagnostic apparatus 100 then measures the distance between the start point and end point to be output as the BPD. The A-P direction and the R-L direction illustrated in FIG. 14 is merely an example and may be reversed in some cases.

In the case of the head, the BPD is measured. In the case of the abdomen, the abdominal circumference is measured. In the case of the feet, the LF is measured. In the cases of the face or the spinal cord, for example, even if still images are captured, the measurement thereof may not be performed. This is why Step S207 is with parentheses.

The ultrasonic probe detection unit 40 detects the position and the angle of the ultrasonic probe 12 put on the abdomen of the mother, similarly to the first embodiment (Step S208). The position specifier 27b specifies the position of the ultrasonic probe 12 on the base image based on the position of the ultrasonic probe 12 detected at Step S208, similarly to the first embodiment. The display controller 27c specifies the position of the region of the fetus ("the head", for example) on the base image based on the measurement information obtained from the measurement at Step S207 ("BPD" measured at Step S207, for example) and the position of the ultrasonic probe 12 thus specified on the base image (Step S209).

Figure 15:
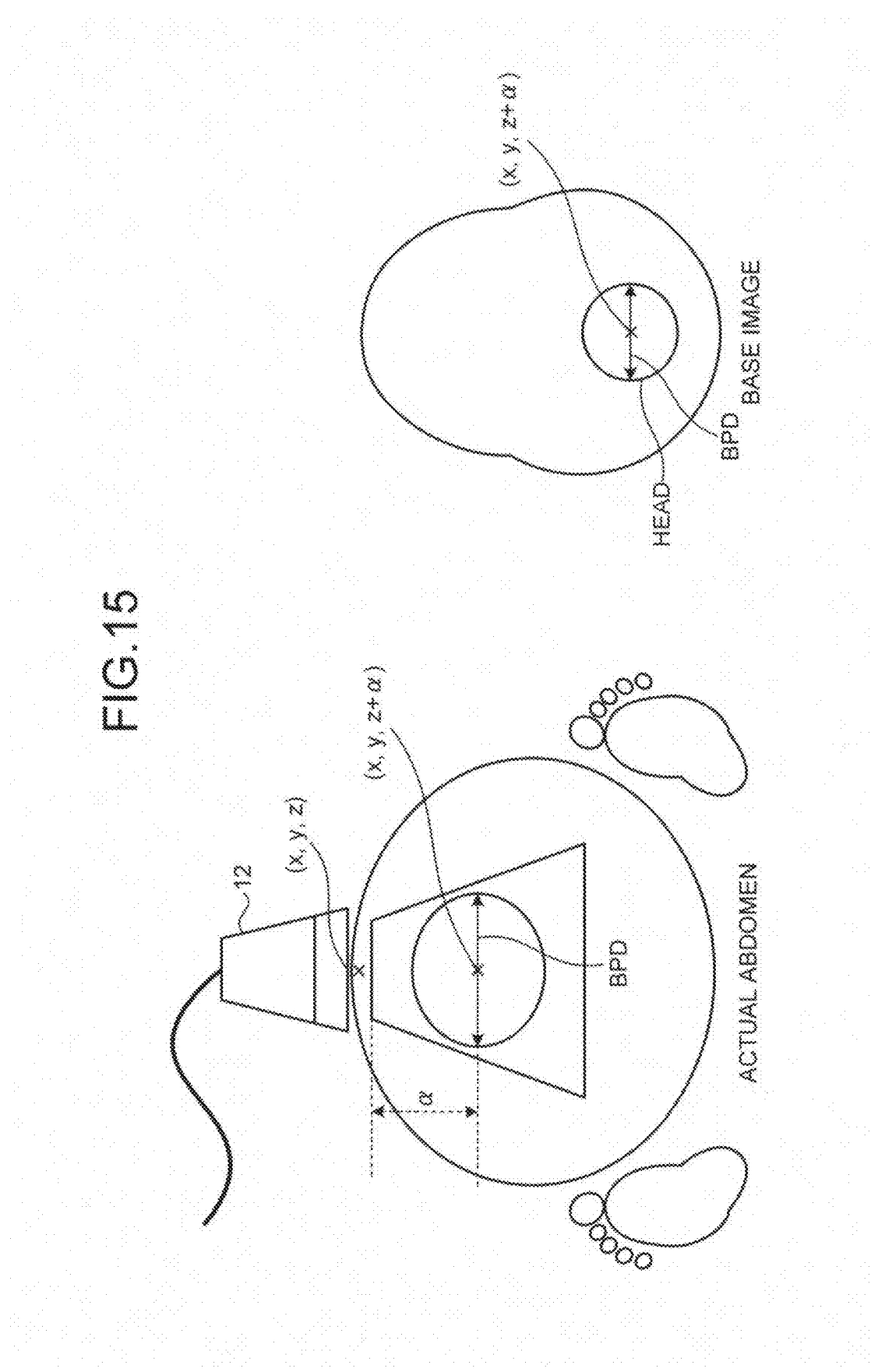
FIG. 15 is a diagram illustrating specification of the position of a fetus according to the second embodiment.

FIG. 15 is a diagram illustrating specification of the position of the fetus according to the second embodiment. For example, the ultrasonic probe detection unit 40 detects the coordinates (x, y, z) as the position of the ultrasonic probe 12, as illustrated in FIG. 15. The depth $\alpha$ of the echo is known. The center of the head of the fetus is positioned in the center of the still image, that is, the position of (x, y, z+$\alpha$). The position specifier 27b specifies the position of (x, y, z+$\alpha$) on the base image, which is the positional information of the still image taken for measuring the BPD. At this point, the position specifier 27b may use the angle detected by the ultrasonic probe detection unit 40. The display controller 27c then places the center of the head on the position corresponding to the position of (x, y, z+$\alpha$) on the base image and specifies the position on which a fetus image depicting the head is to be placed in a manner that the straight line passing the center corresponds to the BPD.

Figure 16:
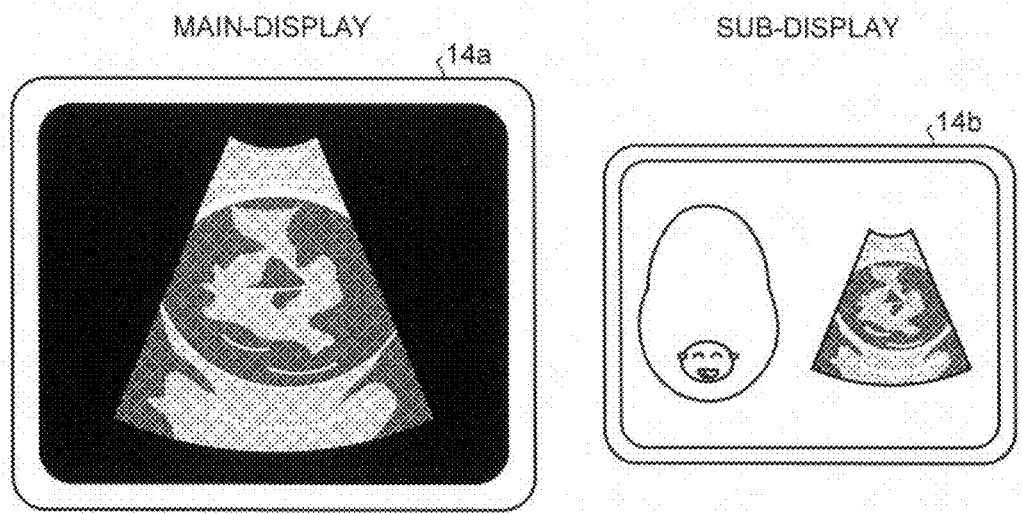
FIG. 16 is a diagram illustrating display of the echo image according to the second embodiment.

Back to FIG. 10, the display controller 27c performs superimposed display of the fetus image for each region on the base image, and causes still images captured corresponding to these fetus images (captured images) to be displayed next to the base image (Step S210). FIG. 16 is a diagram illustrating display of the echo image according to the second embodiment. For example, the display controller 27c causes the subdisplay 14b to perform superimposed display of the fetus image depicting the head on the base image and display the captured head image next to the base image, as illustrated in FIG. 16. At this time, the display controller 27c rotates the fetus image depicting the head in accordance with the A-P direction and the R-L direction of the fetus determined at Step S205 before performing superimposed display thereof on the base image.

The display controller 27c stores therein in advance a three-dimensional fetus image model as a reference of the fetus image for each region measured such as the head, the abdomen, the feet, and the like, and uses this fetus image model as it is as the fetus image for the target region. This fetus image model may be prepared for each average size for each week of pregnancy, for example. The fetus image model may also be prepared only for the head and the abdomen (that is, the abdomen including the feet), for example. The display controller 27c may adjust the size of the fetus image model based on the inputs of BPD, the abdomen circumference, and the FL received as the measurement information, for example.

Figure 17:
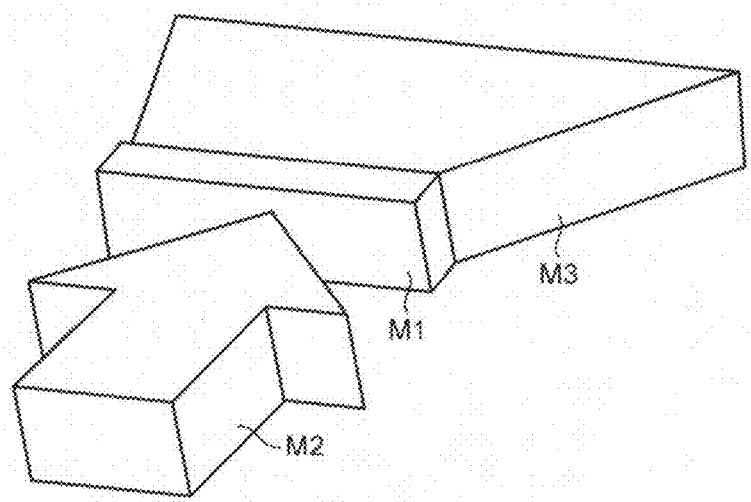
FIG. 17 is a diagram illustrating a probe image according to the second embodiment.

The display controller 27c also performs superimposed display of the probe images on the base image (Step S211). The display controller 27c may store therein a three-dimensional probe image model in advance and use the probe image model. FIG. 17 is a diagram illustrating a probe image according to the second embodiment. In the second embodiment, the probe image is formed by M1 indicating the contact face of the ultrasonic probe 12, M2 indicating the echo direction, and M3 indicating the scanning range, for example. The display controller 27c performs rotation processing of M1, M2, and M3 in a manner that M1, M2, and M3 correspond to the actual contact face, the echo direction, and the scanning range respectively, based on the position, the angle, and the scanning range of the ultrasonic probe 12 specified at Step S208. The display controller 27c then performs superimposed display of the probe image after rotation processing on the position of the ultrasonic probe 12 specified on the base image. The embodiments should not be limited to cases where M1, M2, and M3 are combined for use, but cases where M1, M2, or M3 is used alone may be acceptable. In FIG. 17, a three-dimensional probe image is exemplified. However, the embodiments should not be limited thereto, but a two-dimensional probe image may be used.

As described above, until the echo test is completed (No at Step S212), the processing from Step S206 to Step S211 is repeated for each region of the fetus. FIG. 18 is a diagram illustrating processing of superimposed display according to the second embodiment. As described, the processing from Step S206 to Step S211 is repeated for each region of the fetus, that is, the head (see (1) in FIG. 18), the abdomen (see (2) in FIG. 18), and the feet (see (3) in FIG. 18). In line with the processing, the display controller 27c specifies the position of the head of the fetus, performs superimposed display of the fetus image depicting the head on the base image. The display controller 27c then specifies the position of the abdomen of the fetus and adds superimposed display of a fetus image depicting the abdomen. The display controller 27c then specifies the position of the feet of the fetus and adds superimposed display of a fetus image depicting the feet.

For example, when the center of the abdomen of the fetus is placed on the center of the still image, that is, the position of (x, y, z+α), the position specifier 27b specifies the position of (x, y, z+α) on the base image, which is the positional information of the still image taken for measuring the abdominal circumference. Thereafter, the display controller 27c places the center of the abdomen on the position corresponding to the position of (x, y, z+α) on the base image, and specifies the position on which the fetus image depicting the abdomen is to be placed in a manner that the circumference surrounding the center corresponds to the abdominal circumference. As described above, the display controller 27c performs the fetus image position determination processing for one of the regions of the fetus and sequentially for the other regions generally measured, thereby determining the position of the entire fetus image. In other words, as the measurement of the fetus proceeds, the region parts of the fetus are added, eventually constructing a fetus image for the entire fetus. It should be noted the measurement sequence of the fetus should not be limited to the sequence described above, but an optional sequence may be used for measurement.

Because the A-P direction and the R-L direction have already been determined at Step S205, the display controller 27c rotates the fetus image of each region in accordance with the A-P direction and the R-L direction determined at Step S205 for the display of the fetus image of each region. The orientation of the fetus images for the abdomen and the feet, for example, may be in accordance with the orientation of the head. The H-F direction of the fetus is also specified by specifying the positions of the head and the feet.

Figure 19:
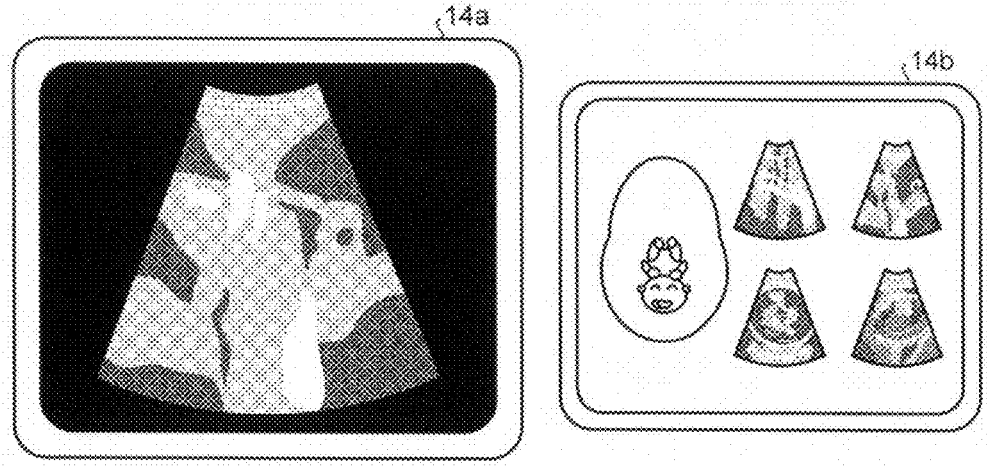
FIG. 19 is a diagram illustrating display of the echo image according to the second embodiment.

FIG. 19 is a diagram illustrating display of the echo image according to the second embodiment. As illustrated in FIG. 19, the display controller 27c causes the subdisplay 14b to perform superimposed display of the fetus image (a fetus image with the head, the abdomen, and the feet combined) and display the still images next to the base image.

As described above, even in the case of a fetus in late pregnancy, which has become so large that the entire body thereof cannot be covered in one screen of the echo image, the ultrasound diagnostic apparatus 100 according to the second embodiment performs superimposed display of the fetus image adjusted to represent the actual position and the orientation on the position corresponding to the actual position on the base image. Therefore, even operators who do not have enough experience of radiogram interpretation can easily grasp the position and the orientation of a fetus in an abdomen. Furthermore, because the probe images are also displayed on the base image according to the second embodiment, it becomes easier for the observer to intuitively grasp the relationship between the still images and the probe.

Third Embodiment

A third embodiment will now be described. In the first embodiment, the description has been principally made based on the assumption of using a two-dimensional echo image generated by two-dimensional scanning. However, the embodiments should not be limited thereto. In the third embodiment, a three-dimensional echo image generated by three-dimensional scanning is assumed. Specifically, superimposed display of a three-dimensional image of the fetus (hereinafter, referred to as "three-dimensional fetus image" as appropriate) extracted from three-dimensional data is performed on the base image graphically representing the abdomen of the mother. It should be noted the three-dimensional image of the fetus is generated as a two-dimensional image on which three-dimensional information is reflected typically by performing rendering processing on the three-dimensional data. The rendering processing includes volume rendering processing, surface rendering processing, and the like.

In general, there are a two-dimensional scanning probe and a three-dimensional scanning probe for the ultrasonic probe 12. As the two-dimensional scanning probe, there is a "one-dimensional array probe" on which a plurality of piezoelectric transducer elements are disposed in line. As the three-dimensional scanning probe, there are a "mechanical four-dimensional probe" and a "two-dimensional array probe". The "mechanical four-dimensional probe" enables two-dimensional scanning by using a plurality of piezoelectric transducer elements disposed in line similarly to a one-dimensional array probe as well as three-dimensional scanning by vibrating a plurality of piezoelectric transducer elements at a predetermined angle. The "two-dimensional array probe" enables two-dimensional scanning by focusing and transmitting ultrasonic waves as well as three-dimensional scanning by using a plurality of piezoelectric transducer elements disposed in a matrix shape.

Figure 20:
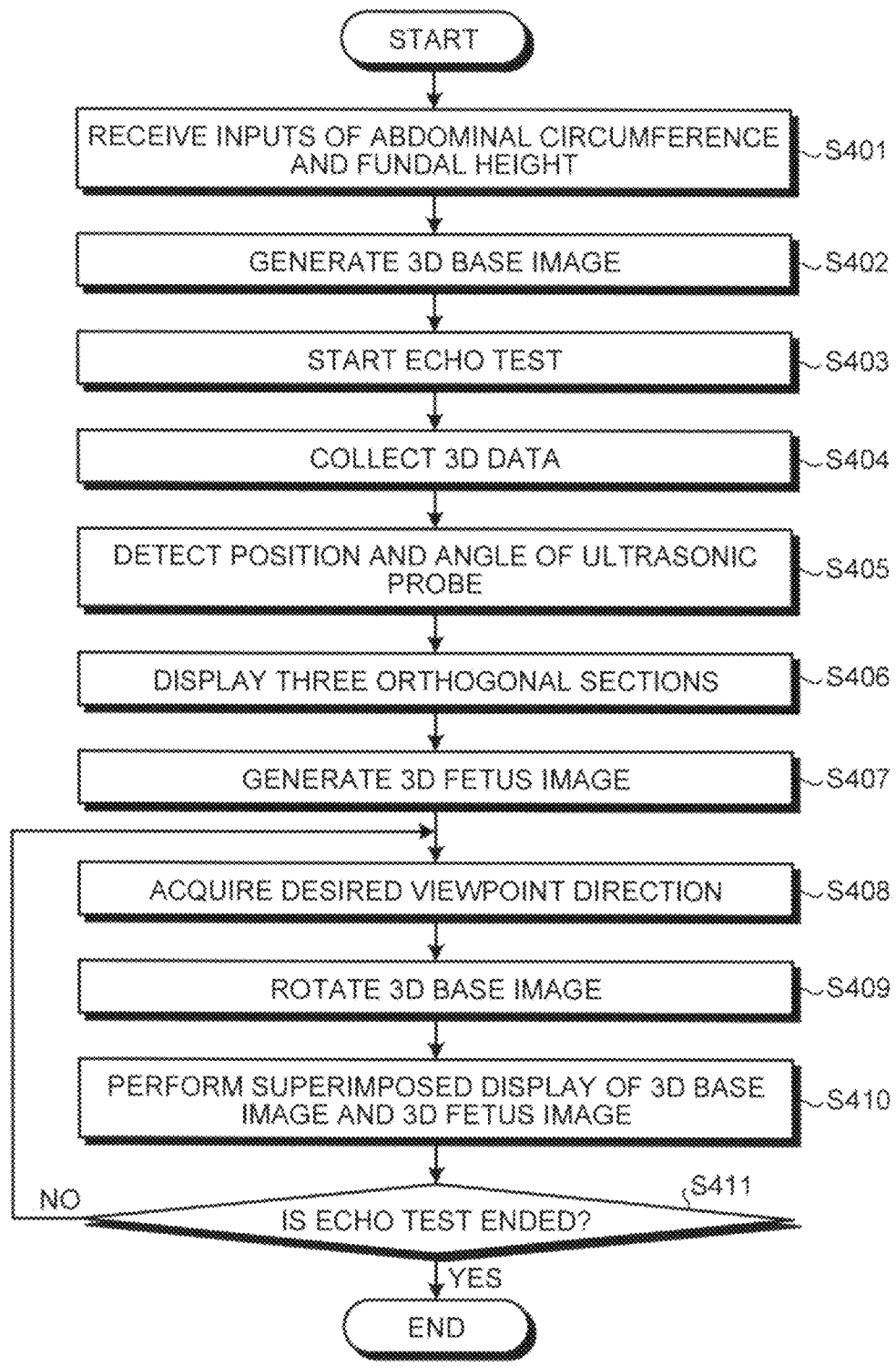
FIG. 20 is a flowchart of the procedure of processing according to a third embodiment.

FIG. 20 is a flowchart of the procedure of processing according to the third embodiment. First, the base image generator 27a receives an input of measurement information of the abdomen of the mother similarly to the first embodiment (Step S401). The base image generator 27a then generates the base image graphically representing the abdomen of the mother based on the input of the measurement information of the abdomen received at Step S401 similarly to the first embodiment (Step S402). In the third embodiment, the three-dimensional fetus image generated by the rendering processing is superimposed on the base image as described later. Therefore, the base image generator 27a generates the base image as a two-dimensional image on which the three-dimensional information is reflected according to the third embodiment. Hereinafter, the base image thus generated will be referred to as "three-dimensional base image".

Next, the echo test performed by the ultrasound diagnostic apparatus 100 is started in accordance with operation performed by the operator (Step S403), and three-dimensional data for the entire fetus is collected (Step S404). In the third embodiment, the operator uses an ultrasonic probe 12 for three-dimensional scanning for the echo test. The control processor 28 controls the ultrasound transmission unit 21 and the ultrasound reception unit 22, thereby collecting three-dimensional raw data. The three-dimensional raw data is processed by the image generation unit 25 to be stored in the image memory 26 as three-dimensional data. The processing performed on the three-dimensional data described below may be performed on the three-dimensional raw data.

Next, the ultrasonic probe detection unit 40 detects the position and the angle of the ultrasonic probe 12 put on the abdomen of the mother similarly to the first embodiment (Step S405). This information is used for the position and scale adjustments between the coordinate system in the space with its origin at the transmitter of the ultrasonic probe detection unit 40 and the coordinate system of the three-dimensional data collected at Step S404. It is assumed that the position and scale adjustments between the coordinate system in the space with its origin at the transmitter of the ultrasonic probe detection unit 40 and the coordinate system on the three-dimensional base image have been completed by prior adjustments using a known technique at this point. In other words, the position and scale adjustments among the coordinate system in the space with its origin at the transmitter of the ultrasonic probe detection unit 40, the coordinate system of the three-dimensional data, and the coordinate system on the three-dimensional base image have been completed.

Figure 21:
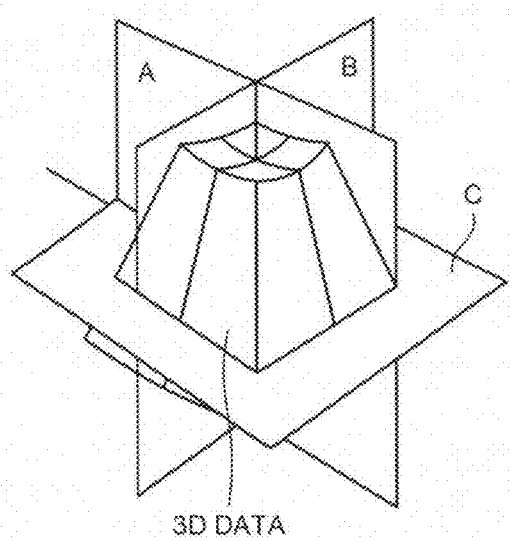
FIG. 21 is a diagram illustrating three orthogonal sections according to the third embodiment.
Figure 22:
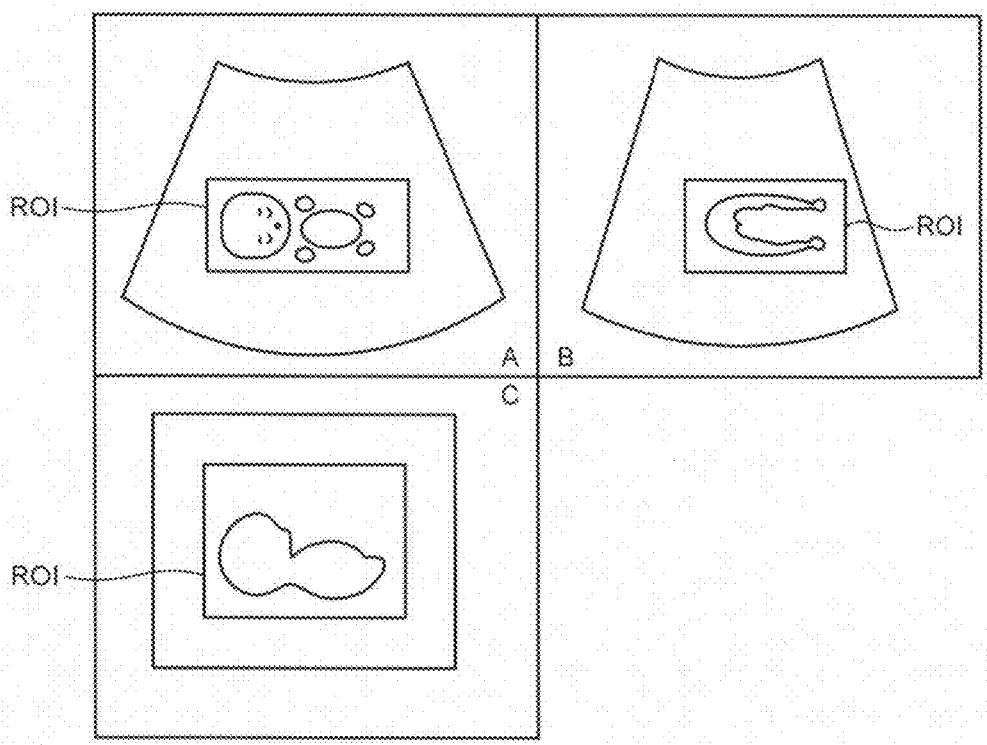
FIG. 22 is a diagram illustrating a setting screen of a region of interest (ROI) according to the third embodiment.

Next, the display controller 27c uses the three-dimensional data collected at Step S404 to cause the main display 14a, for example, to display a region of interest (ROI) setting screen for extracting a region of the fetus from the three-dimensional data thus collected (Step S406). FIG. 21 is a diagram illustrating three orthogonal sections according to the third embodiment. FIG. 22 is a diagram illustrating the ROI setting screen according to the third embodiment.

As illustrated in FIG. 21, the display controller 27c performs multi planar reconstruction (MPR) processing to generate three orthogonal sections A, B, and C with respect to the three-dimensional data, and causes the three orthogonal sections A, B, and C thus generated to be displayed as illustrated in FIG. 22, for example. The three-dimensional data collected at Step S404 generally includes the uterine wall in addition to the fetus. Because there is no significant difference in luminance values between the "fetus" and the "uterine wall", for example, image processing such as threshold processing may be difficult in some cases. Therefore, the display controller 27c according to the third embodiment receives the ROI setting for the "fetus" region from the operator on an MPR image as illustrated in FIG. 22.

Figure 23:
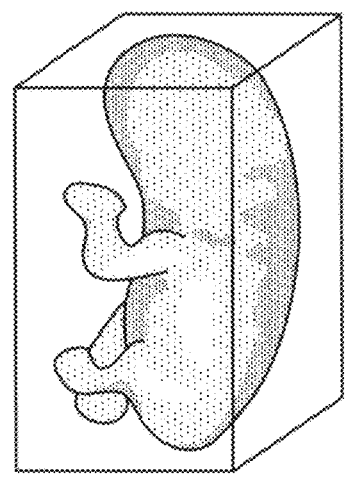
FIG. 23 is a diagram illustrating a three-dimensional image of a fetus according to the third embodiment.

The display controller 27c then performs image processing such as threshold processing for separating the fetus and the amniotic fluid and rendering processing on the three-dimensional data with respect to the ROI region set at Step S406, thereby generating a three-dimensional fetus image (Step S407). FIG. 23 is a diagram illustrating the three-dimensional fetus image according to the third embodiment.

Figure 24:
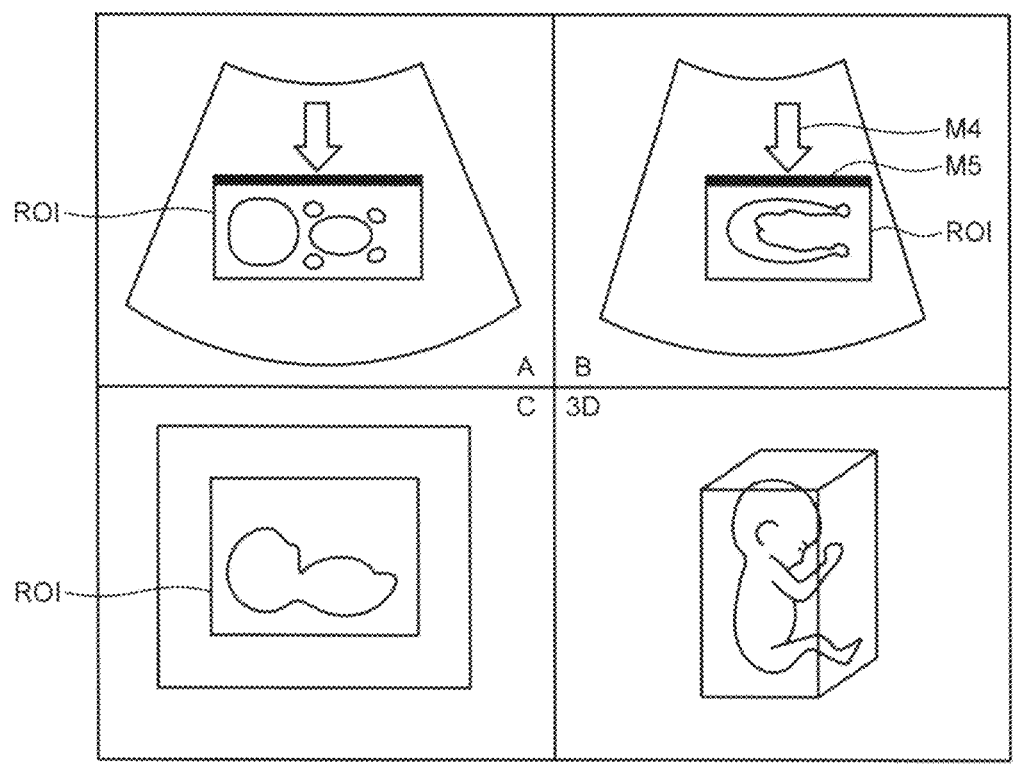
FIG. 24 is a diagram illustrating determination of the direction of a viewpoint according to the third embodiment.

The display controller 27c then arranges the three-dimensional image of the fetus thus generated with the three orthogonal sections as illustrated in FIG. 24, for example. FIG. 24 is a diagram illustrating determination of the direction of a viewpoint according to the third embodiment. On the ROI setting screen illustrated in FIG. 24, there is a region where the three-dimensional image of the fetus is displayed in addition to the three orthogonal sections A, B, and C. For example, when the operator captures using a mouse and rotates the three-dimensional image of the fetus, the display controller 27c causes the above-mentioned region to display the three-dimensional image of the fetus generated by rendering processing in the direction of the viewpoint determined as a result of the rotation operation. On other MPR images, the direction of the viewpoint with respect to the three-dimensional image of the fetus and the displayed surface perpendicular to this direction of the viewpoint are illustrated by arrows and bold lines, as illustrated in FIG. 24. The three-dimensional image of the fetus illustrated in FIG. 23 and the three-dimensional image of the fetus illustrated in FIG. 24 are different for the purpose of explanation. In an actual case, however, the three-dimensional image of the fetus generated at Step S407 is displayed in an optional direction on the ROI setting screen illustrated in FIG. 24.

When the operator rotates the three-dimensional fetus image, for example, to determine the desired direction of the viewpoint (also referred to as viewpoint position, camera position, and the like), the display controller 27c acquires this direction of the viewpoint (Step S408) and rotates the three-dimensional base image generated at Step S402 so as to correspond to the direction of the viewpoint thus acquired (Step S409). Because the position and scale adjustments between the coordinate system of the three-dimensional data and the coordinate system on the three-dimensional base image have been completed, the display controller 27c rotates the three-dimensional base image so as to correspond to the direction of the viewpoint of the three-dimensional fetus image.

Figure 25:
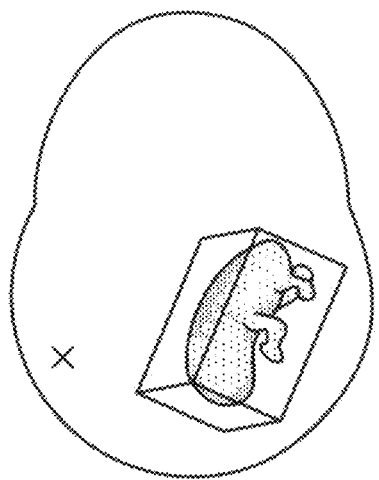
FIG. 25 is a diagram illustrating a displayed image according to the third embodiment.

Thereafter, the display controller 27c performs superimposed (or combined) display of the three-dimensional fetus image in the direction of the viewpoint determined at Step S408 on the three-dimensional base image rotated at Step S409, which is on the position of the ultrasonic probe 12 specified at Step S405 (Step S410). FIG. 25 is a diagram illustrating a displayed image according to the third embodiment. The display controller 27c may cause the main display 14a (in the region for displaying the three-dimensional fetus image illustrated in FIG. 24 or the entire main display 14a, for example) or the subdisplay 14b to display this displayed image with the three-dimensional fetus image superimposed on the three-dimensional base image.

Thereafter, until the echo test is completed (No at Step S411), the processing from Step S408 to Step S410 is repeated. Specifically, when the operator rotates the three-dimensional fetus image to determine the desired direction of the viewpoint, the display controller 27c acquires the direction of the viewpoint of the three-dimensional fetus image and rotates the three-dimensional base image, causing superimposed display of the three-dimensional fetus image after being rotated on the three-dimensional base image after being rotated. The rotation operation of the three-dimensional fetus image performed by the operator may be performed on the ROI setting screen illustrated in FIG. 24 or on the display screen illustrated in FIG. 25.

As described above, according to the third embodiment, superimposed display of the three-dimensional image of the fetus extracted from the three-dimensional data is performed on the three-dimensional base image graphically representing the abdomen of the mother and the three-dimensional base image is rotated to be displayed as the three-dimensional image is rotated. Therefore, even operators who do not have enough experience of radiogram interpretation can easily grasp the position and the orientation of a fetus in an abdomen. Furthermore, when a displayed image as illustrated in FIG. 25 is used for a test at a later stage such as a case where three-dimensional data is imaged in a typical prenatal echo diagnosis before detailed examination of the organs of the fetus is performed, it will become easier even for operators who do not have enough experience of radiogram interpretation to grasp the position of the organ to be next tested. As a result, sections of an organ can be effectively depicted in a typical prenatal echo diagnosis.

In the third embodiment, described has been an example in which processing of collecting three-dimensional data and processing of generation, display, and the like of the three-dimensional fetus image as processing to be performed at a later stage on the three-dimensional data thus collected are performed in a series of procedures. However, the embodiments should not be limited thereto. For example, collection of the three-dimensional data may be performed in advance (in another timing, for example). The processing to be performed at a later stage on the collected three-dimensional data may be performed by an apparatus (an image processing apparatus, for example) other than the ultrasound diagnostic apparatus 100. The generation of the three-dimensional base image and the detection of the position and the angle of the ultrasonic probe 12 may be performed in different timings from the procedure illustrated in FIG. 20. The procedure illustrated in FIG. 20 can be changed optionally in accordance with the form of the operation or other conditions.

Fourth Embodiment

A fourth embodiment will now be described. In the fourth embodiment, the ultrasound diagnostic apparatus 100 extracts an optional section from the three-dimensional data collected in advance and specifies the sectional position in the abdomen with respect to the extracted section. The ultrasound diagnostic apparatus 100 then calculates positional information of the ultrasonic probe 12 for displaying this section and displays the positional information together with the base image.

In recent years, fetal cardiac screening has been prevailing due to high morbidity of cardiac diseases of fetuses. The fetal cardiac screening is performed in the sequence described below. An ultrasonic probe is operated first to grasp the entire image of a fetus. Next, the position of the heart is specified and the image of the cardiac section such as four chamber section is taken. However, many steps may be required before the image of the heart section is taken because there are difficulties involved in taking images of fetuses. For example, the operator first takes the image of the entire body to specify the right and left of the fetus. After the longitudinal face of the spinal column is displayed, the operator changes hands to hold the ultrasonic probe so that the head of the fetus comes in right. The operator further rotates the ultrasonic probe in the counterclockwise direction to display the transverse section, and specifies the spine, thereby specifying the right and left of the fetus (when the spinal column is in the direction of twelve o'clock, the "left" is in the direction of three o'clock and the "right" is in the direction of nine o'clock). After specifying the right and left of the fetus, the operator starts taking images from the abdominal section. The operator gradually translates the ultrasonic probe to the head side in a horizontal manner, eventually taking the image of the heart section. As described above, a lot of time is required before the desired heart section is displayed.

The fetal cardiac screening is preferably performed in a typical prenatal checkup. However, some obstetricians and obstetric nurses do not have enough technical knowledge of cardiology, and there are also the difficulties as described above. In view of this, the ultrasound diagnostic apparatus according to the fourth embodiment can provide the operator with the positional information of the ultrasonic probe for displaying the desired section using the three-dimensional data collected in advance. Described below is an example of providing the position and the angle of the ultrasonic probe (echo incidence angle) for imaging the cardiac section based on the assumption that the heart is a target region of the fetus together with the base image graphically representing the abdomen of the mother. The issue described above may also arise with other regions than the heart. The embodiment described below should not be limited to the heart but also is applicable to other regions.

Figure 26:
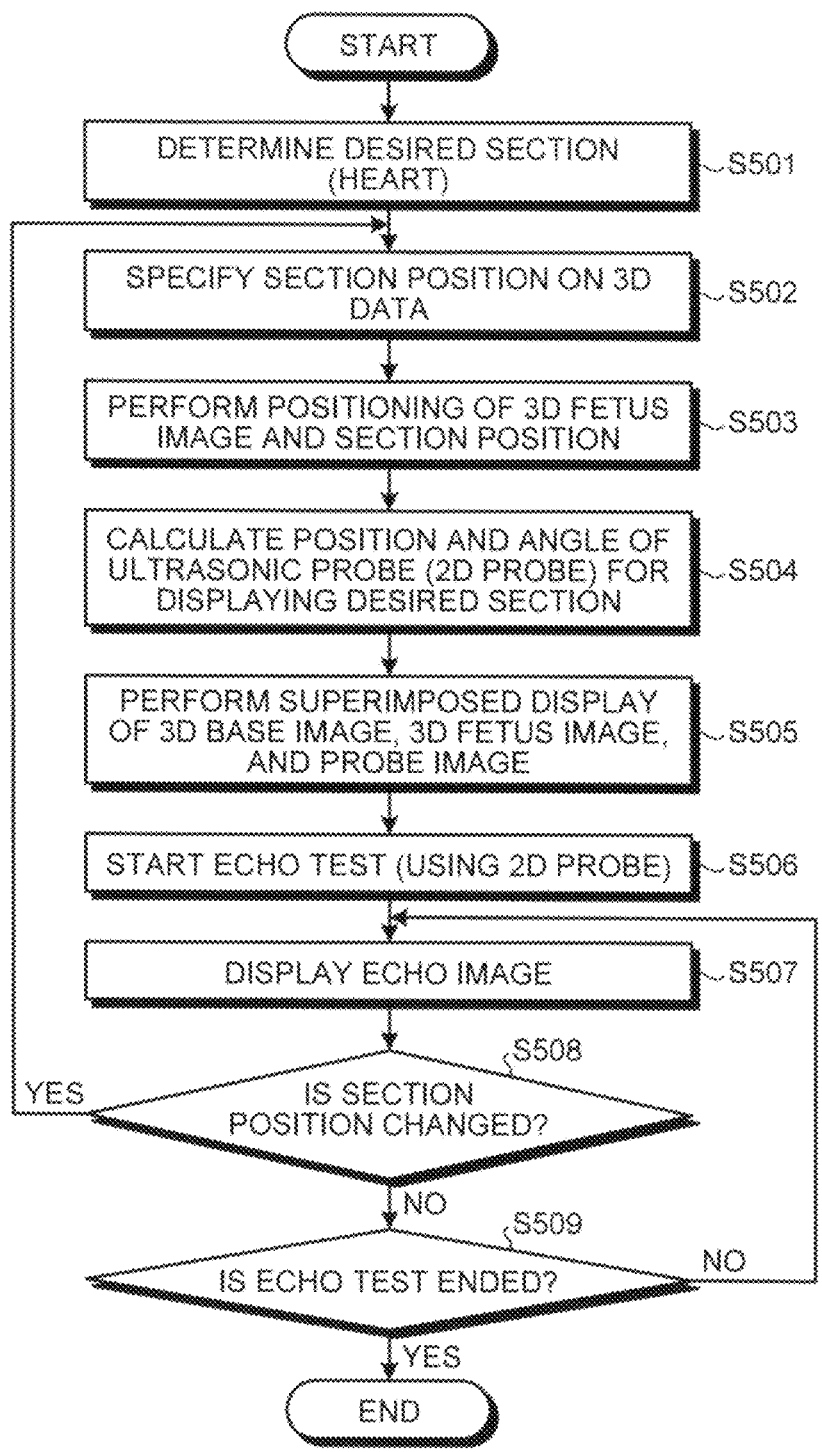
FIG. 26 is a flowchart of the procedure of processing according to a fourth embodiment.

FIG. 26 is a flowchart of the procedure of processing according to the fourth embodiment. Explanation described below is based on the assumption that from Step S401 to Step S410 illustrated in FIG. 20 explained in the third embodiment have been performed before the processing of Step S501 in FIG. 26.

Figure 27:
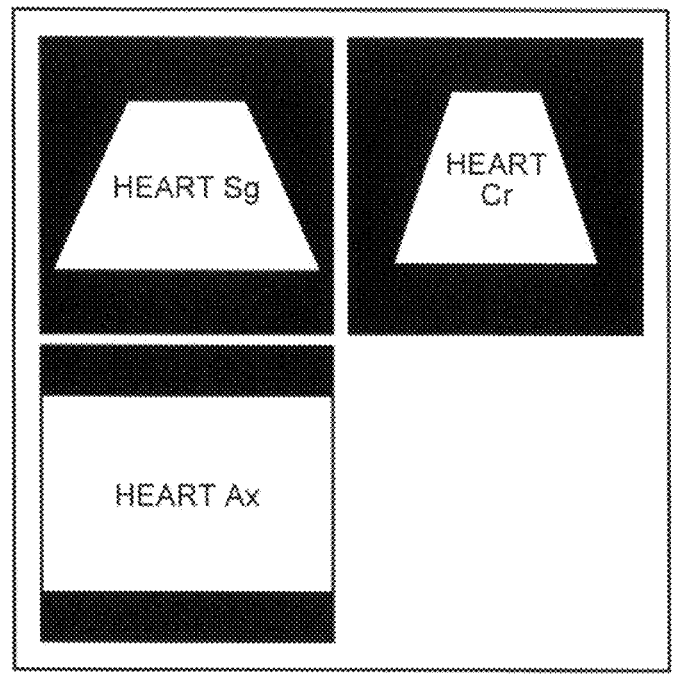
FIG. 27 is a diagram illustrating a displayed screen of three orthogonal sections according to the fourth embodiment.

The display controller 27c uses the screen of the three orthogonal sections displayed on the main display 14a at Step S406 in FIG. 20, for example, to receive the specification of the desired section from the operator, thereby determining the desired section (Step S501). FIG. 27 is a diagram illustrating a displayed screen of three orthogonal sections according to the fourth embodiment. For example, the operator performs operation on the screen of three orthogonal sections to display a sagittal image (heart Sg), a coronal image (heart Cr), and an axial image (heart Ax) as illustrated in FIG. 27. The display controller 27c generates an MPR image from three-dimensional data in accordance with the operation thus received and displays the MPR image thus generated in the screen each time generated. When the operator presses down the "determined" button, for example, in the timing when the desired MPR image is displayed, the display controller 27c determines the MPR image is the desired section.

Figure 28:
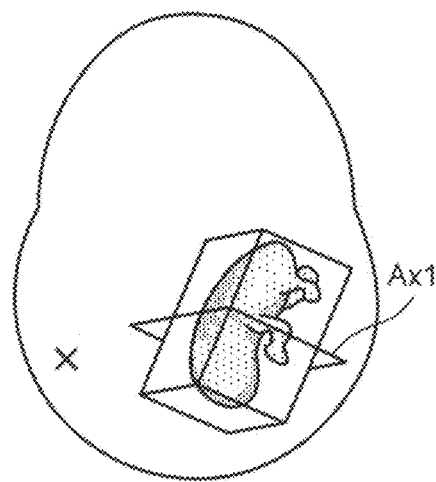
FIG. 28 is a diagram illustrating positioning of a three-dimensional fetus image and a sectional position according to the fourth embodiment.

The display controller 27c specifies the sectional position of the section determined at Step S501 on the three-dimensional data collected at Step S404 in FIG. 20 (Step S502). The display controller 27c also performs positioning between the three-dimensional fetus image and the sectional position (Step S503). FIG. 28 is a diagram illustrating positioning of the three-dimensional fetus image and the sectional position according to the fourth embodiment. For example, the display controller 27c specifies the positional relationship between the three-dimensional fetus image and the desired section Ax1, as illustrated in FIG. 28.

Next, the display controller 27c calculates the position and angle of the ultrasonic probe 12 for displaying the desired section specified at Step S501 (Step S504). In the fourth embodiment, when taking the image of the desired section, it is assumed that an ultrasonic probe 12 (hereinafter, "two-dimensional probe" as appropriate) is used. Therefore, the display controller 27c calculates the position and the angle of the ultrasonic probe 12 as a two-dimensional probe.

Figure 29:
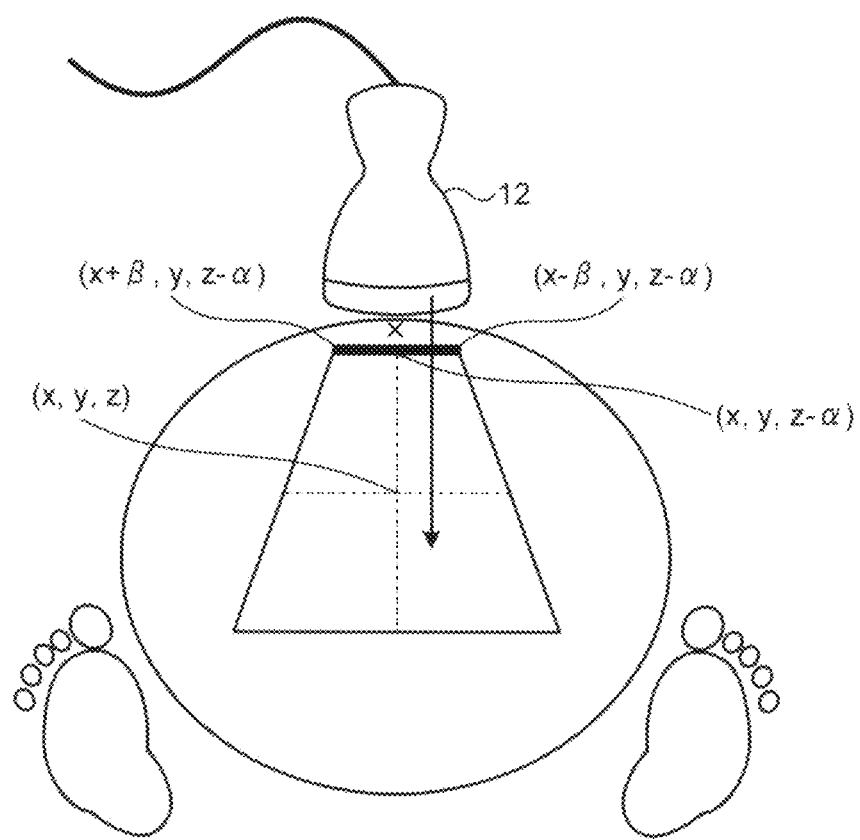
FIG. 29 is a diagram illustrating calculation of the position and the angle of an ultrasonic probe according to the fourth embodiment.

FIG. 29 is a diagram illustrating calculation of the position and the angle of the ultrasonic probe 12 according to the fourth embodiment. For the purpose of explanation, the positional relationship between the actual abdominal of the mother and the range scanned by the ultrasonic probe 12 is illustrated in FIG. 29. When the coordinates of the center of the desired section are (x, y, z) and the depth of the echo is α, the position of the ultrasonic probe 12 is calculated by the coordinates (x+β, y, z−α) and the coordinates (x−β, y, z−α), for example, as illustrated in FIG. 29. In other words, the display controller 27c calculates the coordinates of the both ends of the direction (transverse) where the piezoelectric transducer elements are one-dimensionally arrayed on the ultrasonic probe 12. The angle of the ultrasonic probe 12 is calculated as the direction perpendicular to the transverse direction of the ultrasonic probe 12 (direction of the arrow in FIG. 29).

The display controller 27c then uses the position and angle of the ultrasonic probe 12 calculated at Step S504 to display a probe image further on the displayed image where the three-dimensional fetus image is superimposed on the base image (Step S505).

Figure 30:
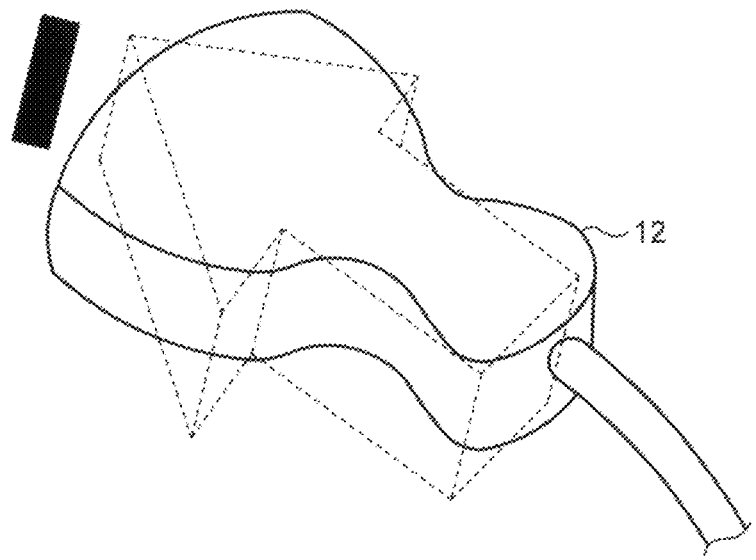
FIG. 30 is a diagram illustrating a probe image according to the fourth embodiment.
Figure 31:
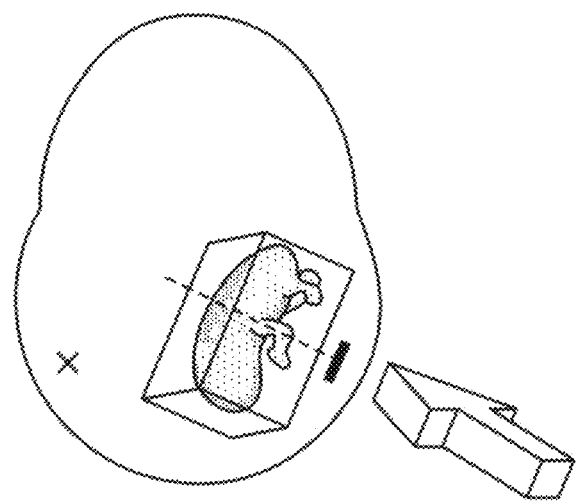
FIG. 31 is a diagram illustrating a displayed image according to the fourth embodiment.

FIG. 30 is a diagram illustrating the probe image according to the fourth embodiment and FIG. 31 is a diagram illustrating the displayed image according to the fourth embodiment. For example, the display controller 27c uses a cubic arrow as a probe image graphically representing the position and the direction of the ultrasonic probe 12, as illustrated in FIG. 30. In FIG. 30, the probe image is illustrated with dotted lines in order to explain the relationship between the ultrasonic probe 12 and the probe image. The display controller 27c also displays a rectangular mark blacked out as illustrated in FIG. 30, as a mark indicating the height direction (the direction in which the piezoelectric transducer elements are two-dimensionally arrayed, vertical direction) of the ultrasonic probe 12. This mark represents the center of the ultrasonic probe 12 in the transverse direction.

The display controller 27c then displays the probe image representing the ultrasonic probe 12 itself, the mark representing the height direction of the ultrasonic probe 12, and the position of the desired section on the displayed image where the three-dimensional fetus image is superimposed on the base image as illustrated in FIG. 31. The display controller 27c may cause the main display 14a (the region in the lower right illustrated in FIG. 27 or the entire main display 14a, for example) or the subdisplay 14b to display this displayed image, for example.

The control processor 28 may calculate at this stage the distance from the ultrasonic probe 12 to the desired section, for example, to derive optimal preset conditions (frequency, for example) for more detailed observation in taking the image of the fetus, and perform automatic adjustment and setting so that the preset conditions thus derived are used for the ultrasonic probe 12 used at a later stage. Naturally, this adjustment can be performed manually by the operator.

Thereafter, the operator changes from the ultrasonic probe 12 to the two-dimensional probe, and puts the ultrasonic probe 12 on the actual abdomen of the mother to start the echo test while observing the displayed image displayed at Step S506 (Step S506). The display controller 27c causes the echo image to be displayed (Step S507).

The display controller 27c also determines if the position of the desired section has been changed on the three orthogonal sections illustrated in FIG. 27 (Step S508). If the position has been changed (Yes at Step S508), the display controller 27c returns to Step S502 where the position of the section is specified on the three-dimensional data. In contrast, when the position of the section has not been changed (No at Step S508) and the echo test is ended (Yes at Step S509), the ultrasound diagnostic apparatus 100 ends the processing.

As described above, according to the fourth embodiment, when the three-dimensional data is imaged in a typical prenatal echo diagnosis before detailed examination of an organ of the fetus is performed, the operator is provided with the position of the ultrasonic probe for imaging the organ to be next tested. Therefore, even operators who do not have enough technical knowledge or experience of screening can effectively image the section of the organ in the typical prenatal echo diagnosis.

Described in the fourth embodiment above has been an example in which a series of procedures of the processing is performed from the procedure of the processing illustrated in FIG. 20 to that illustrated in FIG. 26. However, the embodiments should not be limited thereto. For example, the test at and after Step S506, that is, the test after changing to the two-dimensional probe may be performed in another timing. Furthermore, the procedure of the processing illustrated in FIG. 26 may be changed optionally in accordance with the form of the operation or other conditions.

Other Embodiment

Various embodiments have been described above, but the embodiments should not be limited thereto. For example, three-dimensional echo images may be used instead of two-dimensional echo images in the second embodiment also, as well as in the third and the fourth embodiments. The base image, the fetus image, and the probe image may also be not only two-dimensional but also three-dimensional.

The embodiments described above are based on the assumption that the three-dimensional fetus image, three-dimensional base image, the cubic probe images are mainly generated as two-dimensional images on which three-dimensional information is reflected. However, the embodiments should not be limited thereto. For example, when stereovision is possible on the main display 14a and the subdisplay 14b, the three-dimensional fetus image, the three-dimensional base image, the probe images may be stereovision images.

The embodiment described above is based on the assumption that the base image is mainly generated based on measurement information of the abdomen of the mother. However, the embodiments should not be limited thereto. The base image may be an image prepared as a mere model image.

The embodiments described above also have explained cases where both the position and the angle are calculated as positional information of the ultrasonic probe. However, the embodiments should not be limited thereto. For example, the display controller 27c may calculate only the position as the positional information.

With the ultrasound diagnostic apparatus according to at least one of the embodiments described above, the position and the orientation of a fetus inside an abdomen can be easily grasped.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
an abdominal schema selector that selects an abdominal schema from among abdominal schemas corresponding to different viewpoints, based on an angle of an ultrasonic probe put on an abdomen of a mother, wherein each of the abdominal schemas graphically represents an abdomen of the mother;
an ultrasonic image generator that generates an ultrasonic image based on a reflected wave signal received by the ultrasonic probe;
a specifier that specifies a position of the ultrasonic probe on the abdominal schema; and
a display controller that causes superimposed display of the ultrasonic image on the position on the abdominal schema.

2. The ultrasound diagnostic apparatus according to claim 1, wherein the display controller rotates the abdominal schema in accordance with an orientation of the ultrasonic image superimposed thereon to cause superimposed display of the ultrasonic image on the position on the abdominal schema thus rotated.

3. The ultrasound diagnostic apparatus according to claim 1, wherein, when the ultrasonic image is a two-dimensional image caused by two-dimensional scanning, the display controller rotates the abdominal schema in an orientation observed from a direction perpendicular to a direction of an echo of the ultrasonic probe, and causes superimposed display of the ultrasonic image on the position of the abdominal schema thus rotated.

4. The ultrasound diagnostic apparatus according to claim 1, wherein the display controller displays the abdominal schema so as to arrange the feet or the back on the bottom of the screen.

5. The ultrasound diagnostic apparatus according to claim 1, wherein
the ultrasonic image generator sequentially generates an ultrasonic image in conjunction with a move of the ultrasonic probe,
the specifier sequentially specifies a position of the ultrasonic probe on the abdominal schema in conjunction with the move of the ultrasonic probe, and
the display controller causes superimposed display of an ultrasonic image sequentially generated in accordance with a direction of an echo of the ultrasonic probe on a position on the abdominal schema sequentially specified.

6. The ultrasound diagnostic apparatus according to claim 1, wherein, when the ultrasonic image is a three-dimensional image caused by three-dimensional scanning, the display controller rotates the abdominal schema in an orientation received from an operator as a direction of a viewpoint for displaying the three-dimensional image, and causes superimposed display of the ultrasonic image on the position on the abdominal schema thus rotated.

7. The ultrasound diagnostic apparatus according to claim 1, wherein the abdominal schema generator generates the abdominal schema based on measurement information of an abdomen of a mother.

8. The ultrasound diagnostic apparatus according to claim 1, wherein the display controller causes a second display different from a first display included in an ultrasound diagnostic apparatus body to perform superimposed display of the abdominal schema and the ultrasonic image.

9. The ultrasound diagnostic apparatus according to claim 8, wherein the display controller causes the first display to display the ultrasonic image and causes the second display to perform superimposed display of the abdominal schema and the ultrasonic image.

10. The ultrasound diagnostic apparatus according to claim 8, wherein the display controller causes the second display being a mobile type to perform superimposed display of the abdominal schema and the ultrasonic image.

11. The ultrasound diagnostic apparatus according to claim 1, wherein
the ultrasonic image generator generates a still image of an ultrasonic image,
the specifier specifies a position of the ultrasonic probe when the ultrasonic image is taken, and
the display controller causes superimposed display of the ultrasonic image on the position on the abdominal schema in accordance with a direction of an echo of the ultrasonic probe upon receiving an instruction to display the ultrasonic image.

12. The ultrasound diagnostic apparatus according to claim 1, wherein, when the ultrasonic image is a three-dimensional image caused by three-dimensional scanning, the display controller specifies an optional section based on the three-dimensional image, derives positional information of the ultrasonic probe put on the abdomen for scanning the optional section thus specified, and causes the positional information thus derived to be displayed together with the abdominal schema.

13. The ultrasound diagnostic apparatus according to claim 12, wherein the display controller derives positional information of an ultrasonic probe for two-dimensional scanning as positional information of the ultrasonic probe.

14. The ultrasound diagnostic apparatus according to claim 12, wherein the display controller calculates at least one of a position and an angle of the ultrasonic probe as positional information of the ultrasonic probe.

15. The ultrasound diagnostic apparatus according to claim 12, wherein the display controller causes a probe image graphically representing the ultrasonic probe to be displayed on the abdominal schema when positional information of the ultrasonic probe is displayed together with the abdominal schema.

16. The ultrasound diagnostic apparatus according to claim 1, wherein the display controller rotates the abdominal schema such that an image surface of the ultrasonic image superimposed on the abdominal schema is displayed at a same angle as that of a display surface.

17. An ultrasound diagnostic apparatus, comprising:
an abdominal schema selector that selects an abdominal schema from among abdominal schemas corresponding to different viewpoints, based on an angle of an ultrasonic probe put on an abdomen of a mother, wherein each of the abdominal schemas graphically represents an abdomen of the mother;
an abdominal schema adjuster that adjusts the abdominal schema abdominal schema graphically representing an entire abdomen of a mother based on measurement information of the abdomen of the mother;
an ultrasonic image generator that generates an ultrasonic image with a fetus in the mother imaged based on a reflected wave signal received by the ultrasonic probe;
a specifier that specifies a position of the ultrasonic probe on the abdominal schema, the position of the ultrasonic probe corresponding to when the ultrasonic image is taken; and
a display controller that causes a fetus schema graphically representing the fetus to be displayed on the abdominal schema based on measurement information of the fetus measured using the ultrasonic image and the position of the ultrasonic probe specified on the abdominal schema.

18. The ultrasound diagnostic apparatus according to claim 17, wherein the display controller further causes a probe image graphically representing the ultrasonic probe to be displayed on the abdominal schema.

19. The ultrasound diagnostic apparatus according to claim 17, wherein the display controller specifies an orientation of the fetus in the mother by performing image processing of the ultrasonic image and causes the image of the fetus to be displayed on the abdominal schema in accordance with the orientation thus specified.

20. An ultrasound diagnostic apparatus, comprising:
an abdominal schema selector that selects an abdominal schema from among abdominal schemas corresponding to different viewpoints, based on an angle of an ultrasonic probe put on an abdomen of a mother, wherein each of the abdominal schemas graphically represents an abdomen of the mother;
an ultrasonic image generator that generates a three-dimensional ultrasonic image based on a reflected wave signal received by the ultrasonic probe; and
a display controller that specifies an optional section based on the three-dimensional ultrasonic image, derives positional information of the ultrasonic probe put on the abdomen for scanning the optional section thus specified, and causes the positional information thus derived to be displayed together with the abdominal schema.

* * * * *